US006419927B1

(12) United States Patent
Cerami et al.

(10) Patent No.: US 6,419,927 B1
(45) Date of Patent: *Jul. 16, 2002

(54) METHOD FOR REDUCING ADVERSE EFFECTS OF A HUMAN 70KDA MEDIATOR WHICH RESULTS FROM ENDOTOXIN STIMULATION OF MACROPHAGES

(76) Inventors: Anthony Cerami, Ram Island Dr., Shelter Island, NY (US) 11964; Masanobu Kawakami, 1-2-8 Sendagi Bunkyo-ku, Tokyo 113 (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/345,226

(22) Filed: Nov. 28, 1994

Related U.S. Application Data

(63) Continuation of application No. 07/912,344, filed on Jul. 13, 1992, now abandoned, which is a continuation of application No. 07/283,561, filed on Jul. 15, 1988, now abandoned, which is a division of application No. 06/792,372, filed on Oct. 29, 1985, now Pat. No. 4,822,776, which is a division of application No. 06/414,098, filed on Sep. 7, 1982, now Pat. No. 4,603,106, which is a continuation-in-part of application No. 06/351,290, filed on Feb. 22, 1982, now abandoned, which is a continuation-in-part of application No. 06/299,932, filed on Sep. 8, 1981, now abandoned.

(51) Int. Cl.$^7$ ............................................. A61K 39/395
(52) U.S. Cl. ............................... 424/158.1; 424/145.1; 530/388.23; 530/389.2
(58) Field of Search .......................... 424/145.1, 158.1, 424/130.1; 530/388.23, 389.2; 435/512

(56) References Cited

U.S. PATENT DOCUMENTS

| | | | |
|---|---|---|---|
| 3,300,524 A | 1/1967 | Morris et al. | 260/398.5 |
| 4,003,789 A | 1/1977 | Green | 195/1.8 |
| RE29,169 E | 4/1977 | Schuurs et al. | 195/103.5 A |
| 4,132,769 A | 1/1979 | Osther | 424/1 |
| 4,218,443 A | 8/1980 | Comai et al. | 424/181 |
| 4,242,322 A | 12/1980 | O'Neill | 424/1 |
| 4,309,418 A | 1/1982 | Green | 424/177 |
| RE31,006 E | 8/1982 | Schuurs et al. | 435/7 |
| 4,603,106 A | 7/1986 | Cerami et al. | 435/7 |
| 4,684,623 A | 8/1987 | Larrick et al. | 514/12 |
| 4,870,163 A | 9/1989 | Rubin et al. | 530/412 |
| 5,231,024 A | 7/1993 | Moeller et al. | 435/240.27 |

FOREIGN PATENT DOCUMENTS

| | | | | |
|---|---|---|---|---|
| EP | 0 218 686 A2 | 4/1987 | | C12P/21/02 |
| EP | 0 260 610 A2 | 3/1988 | | C12P/21/00 |
| EP | 0 288 088 A2 | 10/1988 | | G01N/33/68 |
| EP | 0 212 489 B1 | 11/1994 | | C07K/13/00 |
| WO | WO 83/00930 | 3/1983 | | |
| WO | WO 86/06280 | 6/1986 | | |

OTHER PUBLICATIONS

Beutler et al. Nature vol. 320 1986, 584.*
Tracey et. al. J. Exp. Med. vol. 167 1211–1227 1988.*
Harris et al. Tibtech vol 11, 1993 p. 42.*
Biotech Newswatch 1993 p. 2.*
Waldmann Science vol. 252 1657 1971.*
Dorland's Illustrated Medical Dictionary 27th Edition, 1988.*
Verhoef et al Journal of Antimicrobial Chemotherapy vol. 38 167–182, 1996.*
Shim et al., Biological Abstracts (Jan. 15, 1980), vol. 69, No. 2, p. 1164.
Mannel et al., Infection and Immunity (Jul., 1981), 156–164.
Liang et al., Biochemical and Biophysical Research Communications, vol. 137, No. 2 (1986), 847–856.
Hirai et al., Journal of Immunological Methods (1987), vol. 96, 57–62.
Fischer, C. L., et al., II: Serum Protein Abnormalities: Diagnostic and Clinical Aspects, eds. Ritzman, S. E. & Daniels, J. C. (Little Brown, Boston), pp. 331–350. (1975).
Brenneman, D. E., et al., Eur. J. Cancer 11, 225–230. (1975).
Barclay, M., et al., Prog. Biochem. Pharmacol. 10, 76–111, (1975).
Bagby, G. J., et al., Am. J. Physiol. 238, pp. 325–330. (1980).
Rouzer, C. A. et al., Mol. Biochem. Parasitol. 2, 31–38. (1980).
Kawakami, M., et al., J. Exp. Med. 154, 631–639. (1981).
Sipe, J. D., et al., J. Exp. Med. 150, 597–606 (1979).
Kampschmidt, R. F.,et al., J. Lab. Clin. Med. 95:616–623 (1980).
Abraham et al., *JAMA*, 273(12):(Mar. 22/29, 1995) "Efficacy and Safety of Monoclonal Antibody to Human Tumor Necrosis Factor α in Patients With Sepsis Syndrome".
Aggarwal et al., *Methods in Enzymol.,* 116:448–456 (1985) "Human Tumor Necrosis Factor".
Aggarwal et al., *J. Biol. Chem.,* 260(4):2345–2354 (1985) "Human Tumor Necrosis Factor".
Aggarwal et al., *Nature,* 318:665–667 (Dec. 1985) "Characterization of receptors for human tumor necrosis factor and their regulation by γ–interferon".

(List continued on next page.)

Primary Examiner—Lorraine Spector
(74) Attorney, Agent, or Firm—Marshall, Gerstein, & Borun

(57) ABSTRACT

Provided are therapeutic uses of antibodies capable of neutralizing the adverse effects in humans of the about 70 kDa mediator produced upon invasive stimulation of macrophages by, e.g., contact with endotoxin.

8 Claims, 10 Drawing Sheets

OTHER PUBLICATIONS

Atkins et al., *J. Allergy Clin. Immunol. (JACIB)*, 64(4):251–258 (1979) "Further characterization and biologic activity of ragweed antigen–induced neutrophil chemotactic activity in man".

Bach et al., *Immunol. Today,* 14(9):421–425 (1993) "Safety and efficacy of therapeutic monoclonal antibodies in clinical therapy".

Barney et al., Lipton, ed., Fever: International Symposium, Dallas Texas, USA, Apr.11–12, 1979, XII+263P, Raven Press: New York, Illus. ISBN 0–89004–451–1 (08877), 0(0) pp 111–122 (1980) "On the Central Protein Mediator of Fever".

Beisel, *Ann. Rev. Med.,* 26:9–20 (1975) "Metabolic Response To Infection".

Beutler et al., Fed. Proceedings, 44(5):1704 (Abst 7565)(Mar. 8, 1985) "Activated macrophages secrete a novel lipolytic polypeptide hormone".

Beutler et al., *Nature,* 316:552–553 (Aug. 8, 1985) "Identity of tumor necrosis factor and the macrophage–secreted factor cachectin".

Beutler et al., *J. Exp. Med.,* 161:984–995 (May, 1995) "Purification Of Cachectin, A Lipoprotein Lipase–Suppressing Hormone Secreted By Endotoxin–Induced RAW 264.7 Cells".

Beutler et al., *Science,* 229:869–871 (Aug. 1985) "Passive Immunization Against Cachectin/Tumor Necrosis Factor Protects Mice form Lethal Effect of Endotoxin".

Beutler et al., *J. Immunol.,* 135(6):3972–3977 (Dec. 1985) "Cachectin/Tumor Necrosis Factor: Production, Distribution, And Metabolic Fate In Vivo".

Bornstein, et al., 38th Annual National Meeting of the American Federation for Clinical Research, San Francisco, CA USA, Apr. 25–27, 1981, *Clin. Res. (CLREA),* 29(2):381A (1981) "Granulocytosis Induced By Leukocytic Pyrogen Involves A More Proximate Mediator, Granulocytaxin".

Brenneman et al., *Eur. J. Cancer,* 11:225–230 (1975) "Characterization of the Hyperlipidemia in Mice Bearing the Ehrilich Ascites Tumor*".

Bringman, *Hybridoma,* 4(1):85 (1985) "Antigenic distinction between human lymphotoxin and tumor necrosis factor defined with monoclonal antibodies".

Bringman, *Hybridoma,* 6(5):489–507 (1987) "Monoclonal Antibodies to Human Tumor Necrosis Factors Alpha and Beta: Application for Affinity Purification, Immunoassays, and as Structural Probes".

Brown et al., Biochem. Biophys. Res. Commun., 46(2):375–382 (Feb. 1982) "Inhibition Of Lipoprotein By An Apoprotein Of Human Very Low Density Lipoprotein".

Cameron et al., *J. Clin. Invest. (JCINA),* 63(5):977–984 (1979) "Cytotoxicity of Human Macrophages for Tumor Cells".

Carey et al., *J. Clin. Invest,* 34:441–457 (1958) "Studies With Radioactive Endotoxin. III. The Effect Of Tolerance On The Distribution Of Radioactivity After Intravenous Injection Of *Escherichia Coli* Endotoxin Labeled With $CR^{51}$".

Carr et al., *J. Clin. Endocrinol. Metab. (JCEMA),* 52(6):1124–1128 (1981) "The Role of Cyclic Adenosine 3',5'–Monophosphate in Cholesterol Metabolism and Steroidogenesis by the Human Fetal Adrenal Gland*".

Carswell et al., Proc. Natl. Acad. Sci. (USA), 72(9):3666–3670 (Sep. 1975) "An endotoxin–induced serum factor that causes necrosis of tumors".

Cerami et al., Immunol. Letters, 11:173–177 (1985) "Weight Loss Associated With An Endotoxin–Induced Mediator From Peritoneal Macrophages: The Role Of Chachetin (Tumor Necrosis Factor)".

Chang et al., *J. Biol. Chem. (JBCHA),* 256(12):6174–6180 (1981) "Evidence Indicating that Inactivation of 3–Hydroxy–3–methylglutaryl Coenzyme A Reductase by Low Density Lipoprotein or by 25–Hydroxycholesterol Requires Mediator Protein(s) with Rapid Turnover Rate*".

Chaudry et al., *Arch. Surg.,* 109:412–415 (1978) "Insulin Resistance in Experimental Shock".

Cohen, *Am J. Pathol. (AJPAA),* 88(3):502–528 (1977) "The Role of Cell–Mediated Immunity in the Induction of Inflammatory Responses".

Coleman et al., *J. Biol. Chem.,* 253:7256–7261 (1978) "Selective Changes in Microsomal Enzymes of Triacylglycerol Phosphatidylcholine, and Phosphatidylethanolamine Biosynthesis during Differentiation of 3T3–L1 Preadipocytes*".

*Dale et al., *Scientific American Machine,* Sec. 9. Ch. II, pp. 1–6 (1996).

Dayer et al., *J. Exp. Med.,* 162:2163–2168 (Dec. 1985) "Cachectin/Tumor Necrosis Factor Stimulates Collagenase And Prostaglandin $E_2$ Production By Human Synovial Cells And Dermal Fibroblast".

Dinarello, FASEB J., 2:108–115 (1988) "Biology of Interleukin I".

Dinarello et al., Inflammation, 6:63–78 (1982) "Studies On The Active Site Of Human Leukocyte Pyrogen".

Dinarello, *Fed. Proc.,* 38:52–56 (1979) "Production of endogenous pyrogen".

Dinarello et al., J. Clin. Invest., 60:465–472 (1977) "The Production of Antibody against Human Leukocyte Pyrogen".

Dinarello et al., Proc. Nat'l. Acad. Sci. (USA), 74(10):4624 (1977) "Human Leukocyte Pyrogen: Purification And Development Of A Radioimmunoassay".

Dinarello, *Reviews of Infectious Diseases,* 6(1):(Jan.–Feb. (1984) "Interleukin–I".

Dinarello, The Year In Immunology, 2:68–89 (1986) "Interleukin–1: Amino Acid Sequences, Multiple Biological Activities and Comparison with Tumor Necrosis Factor (Cachectin)".

Doerrler et al., *Cytokine,* 6(5):478–484 (Sep. 1994) "Cytokines Induce Catabolic effects in Culture Adipocytes By Multiple Mechanisms".

Dorland's Illustrated Medical Dictionary 27th Edition (1988) "Antitoxin".

Eckel et al., *Biochem. Biophys. Res. Commun.,* 78:288–93 (1977) "Development Of Lipoprotein Lipase In Cultured 3T3–L1 Cells".

Eckel et al., *Biochem. Biophys. Res. Commun.,* 84(4):1069–1075 "Insulin Regulation Of Lipoprotein Lipase In Cultured 3T3–L1 Cells".

Edelson et al., *J. Exp. Med.,* 142:1150–1164 (1975) "The Pinocytic Rate Of Activated Macrophages*".

Exley et al., The Lancet, 335, 1275–1277 (1990) "Monoclonal antibody to TNF in severe septic shock".

Farshtchi et al., *J. Bacteriol.,* 95:1615 (1968) "Effects of Three Bacterial Infections on Serum Lipids of Rabbits".

Fendly et al., *Hybridoma*, 6(4):359–370 (1987) "Murine Monoclonal Antibodies defining Neutralizing Epitopes on Tumor Necrosis Factor".

Fielding et al., *Arch. Pathol. Lab Med.*, 101:225–229 (1977) "Lipoprotein Lipase".

Fransen et al., *Nucleic Acids Research*, 13(12):4417–4429 (1985) "Molecular cloning of mouse tumour necrosis factor cDNA and its eukaryotic expression".

Frayn, *Europ. J. Clin. Invest.*, 5:331–337 (1975) "Effects of Burn Injury on Insulin Secretion and on Sensitivity to Insulin in The Rate in vivo".

Galfré et al., *Nature*, 277:131–133 (Jan. 11, 1979) "Rat x rat hybrid myelomas and a monoclonal anti–Fd portion of mouse IgG".

Gallagher et al., *Abstr. Annu. Meet. Am. Soc. Microbiol* (*AMAC*), 79:64 (1979).

Gallin et al., *Cell Immunol.* (*CLIMB*), 27(2):348 (1976) "Electrophysiology of human Macrophage Stimulation by Endotoxin Activated Serum".

Gallin et al., *N. Engl. J. Med.*, 281:1081 (1969) "Serum Lipids In Infection*".

Goding, Monoclonal Antibodies:Principles and Practice Academic Press, Inc. pp. 78–85 (1983) "Production and Application of Monoclonal Antibodies in cell Biology, Biochemistry and Immunology".

Green et al., *Cell*, 1:113–116 (1974) "Sublines of Mouse 3T3 Cells That Accumulate Lipid".

Green et al., *Cell*, 5:19–27 (1975) "An Established Preadipose Cell Line and its Differentiation in Culture II. Factors Affecting the Adipose Conversion".

Green et al., *Cell*, 7:105–113 (1976) "Spontaneous Heritable Changes Leading to Increased Adipose Conversion in 3T3 Cells".

Grossberg et al., *Nature*, 208:954 (1965) "Hyperlipaemia Following Viral Infection In The Chicken Embryo: A New Syndrome".

Hahn et al, *Proc. Natl. Acad. Sci. (USA)*, 82:3814–3818 (Jun. 1985) "Use of monoclonal antibodies to a human cytotoxin for its isolation and for examining the self–induction of resistance to this protein".

Haidaris et al., *Infect. Immun.*, 42(1):385–393 (Oct. 1983) "Serum Containing Tumor Necrosis Factor Is Cytotoxic for the Human Malaria Parasite *Plasmodium flaciparum*".

Harpers Collin's Illustrated Medical Dictionary, pp. 80 and 434 (1993).

Haranaka et al., *Int. J. Cancer*, 36:395–400 (1985) "Purification And Partial Amino Acid Sequence Of Rabbit Tumor Necrosis Factor".

Havel et al., *J. Clin. Invest*, 39:1777 (1960) "Idiopathic Hyperlipemia: Metabolic Studies In An Affected Family*".

Herring et al., *J. Clin. Invest*, 42:79 (1963) "Distribution and Clearance of Circulating Endotoxin*".

Hiller et al., *Haemostasis*, 6:347–350 (1977) "Procoagulant Activity of Activated Monocytes".

Hirsh et al., *J. Lipid Res.*, 5:563–568 (1964) "Hyperlipidemia, fatty liver, and bromsulfophthalein retention in rabbits injected intravenously with bacterial endotoxins".

Hotez et al., *Parasite Immunol.*, 6:203–209 (1984) "Lipoprotein lipase suppression in 3T3–L1 cells by a Haematoprotozoan–induced mediator from peritoneal exudate cells".

Hoffman–Goetz et al., *Am. J. Clin. Nutr.* (*AJCNA*), 32(7):1423–1427 (1979) "Protein deficiency: its effects on body temperature in health and disease states[1–4]".

Hughes et al., *J. Biol. Chem.*, 256(2):664–671 (Jan. 25, 1981) "Characterization of Plasma Membrane Proteins Identified by Monoclonal Antibodies".

Itkin et al., *J. Allergy* (*JOALA*), 41(2):88–89 (1968) "The role of atropine as a mediator blocker of Induced bronchial obstruction".

Johnson et al., *Cell Immunol.* (*CLIMB*), 44(1):125–130 (1979) "Suppression of in Vitro Antibody Response by Ribosome–Associated Factor(s) from Interferon–Treated Cells".

Johnson et al., *IRCS Int. Res. Commun. Syst. Med. Sci. Libr. Compend.* (*IRLCA*), 4(5):187 (1976) "Interferon As The Mediator Of The Suppressive Effect Of Some Interferon Inducers In The In Vitro Immune Response".

Juniper et al., *Clin Allergy* (*CLAGB*), 11(1):61–66 (1981) "Effects of oxatomide compared with chlorpheniramine in allergic rhinoconjunctivitis".

Kaliner, *Am. Rev. Respir. Dis* (*ARDSB*), 118 (6 Part 1), (Received 1979) pp 1015–1022 (1978) "Human Lung Tissue and Anaphylaxis: The Effects of Histamine on the Immunologic Release of Mediators".

Kampschmidt, *Ann. Okla. Acad. Sci.* (*AOASA*), 4:62–67 (Received 1975) (1974) "Effects Of Leukocytic Endogenous Mediator on Metabolism And Infection".

Kampschmidt et al., (eds.) FEVER:International Symposium, Dallas, Texas USA, Apr. 11–12, 1979, XII+263P, Raven Press:New York, USA Illus. ISBN 0–89004–451–1 (08877) 0(0) pp. 49–56 (1980) "Metabolic Alterations Elicited by Endogenous Pyrogens".

Kampschmidt et al., *Microbiology*, (Washington, DC):1980)IX+4000P, American Society for Microbiology: Washington, DC, USA, Illus. ISBN 0–914826–23–9 (MICRD), 0(0), 150–153 (1980) "Biological Manifestations of Leukocytic Endogenous Mediator".

Kampschmidt, *J. Reticuloendothel, Soc.*, 23:287–297 (1978) "Leukocytic Endogenous Mediator".

Kampschmidt et al., *J. Reticuloendothel. Soc.* (*RESJA*), 28(2):191–202 (1980) "Neutrophil Release After Injections of Endotoxin or Leukocytic Endogenous Mediator into Rats".

Kawakami et al., Proc. Natl Acad Sci (USA), 79(2):912–916 (1982) "Lipoprotein lipase suppression in 3T3–L1 cells by an endotoxin–induced mediator from exudate cells".

Kawakami et al., IUPHAR 9th International Congress of Pharmacology, Proceedings, vol. 2, (London 1984), The Macmillan Press Ltd., pp. 377–384 "Studies of Conditions and agents that stimulate and inhibit the production of cachectin by macrophages".

Kawakami et al., *J. Biochem.*, 101:331–338 (1987) "Human Recombinant TNF Suppresses Lipoprotein Lipase Activity and Stimulates Lipolysis in 3T3–L1 Cells".

Kearney et al., *J. Immunol.*, 123(4):1548–1550 (Oct. 1979) "A New Mouse Myeloma Cell Line That Has Lost Immunoglobulin Expression But Permits The Construction Of Antibody–Secreting Hybrid Cell Lines".

Keenan et al., 65th Annual Meeting of the Federation of American Societies for Experimental Biology, Atlanta, GA USA, Apr. 12–17, 1981, *Fed. Proc.* (*FEPRA*), 40(3 Part 1):439 (1981) "Human And Rabbit Leukocyte Endogenous Mediator (LEM) Produces Similar Responses In The Restrained Rat".

Kelker et al., *Int. J. Cancer*, 36:69–73 (1985) "Characterization of Human Tumor Necrosis Factor Produced By Peripheral Blood Monocytes and Its Separation From Lymphotoxin".

Kempf et al., *J. Immunol. (JOIMA)*, 119(2):517–523 (1977) "Transient Suppression Of The Humoral Immune Response Mediated By A Factor Derived From Specifically Activated, Doubly Primed Lymphoid Cells".

Kennerly et al., *J. Immunol. (JOIMA)*, 122(1):152–159 (1979) "Activation Of Phospholipid Metabolism During Mediator Release From Stimulated Rat Mast Cells".

Khan et al., *Exp. Hematol*, 20:900–903 (1992) "Effects of Tumor Necrosis FActor–alpha on Normal Feline Hematopoietic Progenitor Cells".

Koda et al., *JAP. J. Allergol. (ARERA)*, 22(1):33–34 (1973) (in Japanese—no translation).

Köhler, *Hybridoma*, 1(1):1–4 (Nov. 1, 1981) "Why Hybridomas?".

Köhler et al., Nature, 256:495–497 (Aug. 7, 1975) "Continuous cultures of fused cells secreting antibody of pre-defined specificity".

Korn, *J. Biol. Chem.*, 215:1–14 (1955) "Clearing Factor, A Heparin–Activated Lipoprotein Lipase, I. Isolation and characterization of the enzyme from normal rat heart".

Korn, *J. Biol. Chem.*, 215:15–26 ((1955) "Clearing Factor, A Heparin–Activated Lipoprotein Lipase, III. Substrate specificity and activation of coconut oil".

Krejci et al., *Folia Microbiol. (FOMIA)*, 13(6):562 (1968) "Demonstration of Inflammatory Activity of a Substance Released during Incubation of Lymph Node Cells from Hypersensitive Animals with a Large Dose of Antigen".

Kull et al., *Proc. Natl. Acad. Sci. (USA)*, 81:7912–7936 (Dec. 1984) "Necrosin:Purification and properties of a cytotoxin derived form a murine macrophage–like cell line".

Lennon et al., *Nature*, 285:238 (May 22, 1980) "Myastenia gravis induced by monoclonal antibodies to acetylcholine receptors".

Levy et al., *Monoclonal Antibodies: A New Dimension in Biological Analysis*, Kennett et al. (eds.), Plenum Press, New York, pp. 137–153 "Mouse X Human Hybridomas".

Mackall et al., *J. Biol. Chem.*, 251:6462–6464 (1976) "Induction of Lipogenesis during Differentiatin in a 'Preadipocyte' Cell Line".

Mahoney, Jr., et al., *J. Immunol.*, 134(3):1673–1675 (1985) "Lipopolysaccharide–Treated Raw 264.7 Cells Produce A Mediator That Inhibits Lipoprotein Lipase in 3T3–L1 Cells".

Man et al., *J. Clin. Invest.*, 24:623 (1945) "The Lipids of Serum and Liver in Patients with Hepatic Diseases".

Männel et al., Infect. Immun., 30:523–530 (1980) "Macrophages as a Source of Tumoricidal Activity (Tumor–Necrotizing Factor)".

Mapes et al., *Fed. Proc. (FEPRA)*, 36(3):1138 (1977) "Zinc Ion Inhibition Of Prostaglandin Synthesis And Leukocytic Endogenous Mediator (LEM) Production".

Marmenout et al., *Biochem.*, 152:515–522 (1985) "Molecular cloning and expression of human tumor necrosis factor and comparison with mouse tumor necrosis factor".

Matthews, *Immunology*, 48:321–327 (1983) "Effect of human monocyte killing of tumour cells of antibody raised against an extracellular monocyte cytotoxin".

Mauer et al., *Methods Enzym.*, 70:49–70 (1980) Academic Press, "Proteins and Polypeptides as Antigens".

*Mayer, *Med. Presma. (MZPRA)*, 5:5–36 (1975).

McAdam et al., *Lancet, II*:572–575 (Sep. 1975) "Association Of Amyloidosis With Erythema *Nodosum Leprosum* Reactions and Recurrent Neutrophil Leucocytosis In Leprosy".

McGrath et al., *Nature*, 285:259–261 (May 22, 1980) "Murine leukaemogenesis: monoclonal antibodies to T–cell determinants arrest T–lymphoma cell proliferation".

Meager et al., *Hybridoma*, 6(3):305–311 (1987) "Preparation and Characterization of Monoclonal Antibodies Directed Against Antigenic Determinants of Recombinant Human Tumour Necrosis Factor (rTNF)".

Melchers et al., Lymphocyte Hybridomas, eds. Melcher et al., Springer–Verlag, (NIH—Apr. 3–5, 1978), p. IX–XXXIII (1979) "Second Workshop on Functional Properties of Tumours of T and B Lymphocytes".

Merck Index (The), 10th Ed. Windholz ed. No. 5339 (1983) "Lipoprotein Lipase".

Merriman et al., *Proc. Soc. Exp. Biol. Med. (PSEBA)*, 154(2):224–227 (1977) "Comparison of Leukocytic Pyrogen and Leukocytic Endogenous Mediator (39642)".

Michalek et al., *Fed. Proc. (FEPRA)*, 38(3 Part 1):1284 (1979) "Cellular and Soluble Mediator Requirements For Lipopolysaccharide (LPS)–Induced Enhancement of Antibody Responses".

Miller et al., *Infect. Immun.*, 57(5):1542–1546 (1989) "Tumor Necrosis Factor Alpha and the Anemia Associated with Murine Malaria".

Morii et al., *J. Biol. Chem.*, 258(21):12749–12752 (Nov. 10, 1983) "Amino Acid Sequence at the Reactive Site of Human $\alpha_1$–Antichymotrypsin".

Murphy et al., J. Immunol., 124(1):2498–2501 (May, 1980) "Endogenous Pyrogens Made By Rabbit Peritoneal Exudate Cells Are identical With Lymphocyte–Activating Factors Made By Rabbit Alveolar Macrophages".

Newborg et al., *Infec. Immun. (INFIB)*, 24(3):667–672 (Jun., 1979) "Suppressive Effect of Bacterial Endotoxin on the Expression of Cell–Mediated Anti–Listeria Immunity".

Nillson–Ehle et al., *J. Lipid Res.*, 17:536–541 (1976) "A Stable, radioactive substrate emulsion for assay of lipoprotein lipase".

Okpako, *Int. Arch. Allergy*, 40:620–630 (1971) "The Effect of Graded Doses of Antigen on Bronchoconstrictor and Mediator–Release Responses in Anaphylaxis of the Isolated Perfused Guinea–Pig Lung".

Olivecroma et al., *Fed. Proc. Fed. Am. Soc. Exp. Biol*, 36(1):6065 (Jan., 1977).

Parrillo, *The New Eng. J. Med.*, 328:1471–1477 (1993) "Pathogenetic mechanisms of Septic Shock".

Paterson et al., *Pneumologie (PNMGA)*, 153(2):148 (1976) "Chemical Mediator Release From Lung Cells".

Paterson et al., *Fed. Proc. (FEPRA)*, 35(3):865 (1976) "Mediator Release From Human Lung Cells Distributed According To Density".

Pekala et al., Proc. Natl. Acad. Sci. (USA), 80:2743–2747 (May, 1983) "Selective inhibition of synthesis of enzymes for de novo fatty acid biosynthesis by an endotoxin–induced mediator from exudate cells".

Pennica et al., *Nature*, 312:724–728 (1984) "Human tumour necrosis factor: percursor structure, expression and homology to lymphotoxin".

Pennica et al., *Proc. Natl. Acad. Sci. (USA)*, 82:6060–6064 (Sep. 1984) "Cloning and expression in *Escherichia coli* of the cDNA for murine tumor".

Pennington, *ASM News* 58(9):479–482 (1992) "TNF: Therapeutic Target in Patients with Sepsis".

Peterson et al., *Diabetes*, 26:507–509 (May, 1977) "Correlation of Serum Triglyceride Level and Hemoglobin $A_{Ic}$ Concentrations in Diabetes Mellitus".

Plescia, *Cell Immunol.*, (*CLIMB*), 27(2):348–349 (Received 1977) (1976) "Immediate Cyclic AMP Response to Antigen–Manifestation of Release of Mediator(s) from Specific Antigen–Sensitive Cells".

Pykälistö et al., *J. Clin. Invest.*, 56:1108–1117 (1975) "Determinants of Human Adipose Tissue Lipoprotein Lipase".

Pykälistö et al., *Proc. Soc. Exp. Biol. Med.*, 148:297 (1975) "Human Adipose Tissue Lipoprotein Lipase:Comparison of Assay Methods and Expression of Activity (38526)".

Ralph et al., *J. Immunol.*, 119(3):950–954 (1977) Antibody–Dependent Killing Of Erythrocyte And Tumor Targets By Macrophage–Related cell Lines:Enhancement By PPD and LPS.

Ranges et al., *J. Exp. Med.*, 167:1472–1478 (1988) "Tumor Necrosis Factor α/Cachectin Is A Growth Factor For Thymocytes—Synergistic Interactions with Other Cytokines".

Rhein, *Bio. Technology Newswatch*, pp. 1–3 (Oct. 4, 1993) "Another Sepsis drug down Immunex' TNF receptor".

Ritz et al., *Nature*, 283:583–584 (Feb. 7, 1980) "A monoclonal antibody to human acute lymphoblastic leukaemia antigen".

Rosenthal et al., *J. Clin. Invest.*, 55:746 (Apr., 1975) "Variation with Age and Disease of an Amyloid A Protein–Related Serum Component".

Rubin et al., *J. Biol. Chem.*, 253:7570–7578 (Oct. 5, 1978) "Development of Hormone Receptors and Hormonal Responsiveness in Vitro".

Rudinger et al., *Peptide Hormones*, Parsons ed., Univ. Park Press, Baltimore, pp. 1–7 (1976) "Characteristics of the amino acids as components of a peptide hormone sequence".

Ruff et al., *J. Immunol.*, 125(4)1671–1677 (1980) "Purification and Physico–Chemical Characterization Of Rabbit Tumor Necrosis Factor".

Ruff et al., *Lymphokines*, 2:235–272 (1981) "Tumor Necrosis Factor ".

Rusten et al., *Blood*, 85(4):989–996 (Feb. 15, 1995) "Tumor Necrosis Factor (TNF)–α Directly Inhibits Human Erythropoiesis In Vitro: Role of p. 55 and p. 75 TNF Receptors".

Sakaguchi et al., *Microbiol. Immunol.*, 23(2):71–85 (1979) "Alterations of Lipid Metabolism in Mice Injected with Endotoxin".

Schall, Jr. et al., *Clin. Chem.*, 27(7):1157–1164 (1981) "Alternative to Radio immunoassay: Labels and Methods".

Selvam et al., *INDIAN J. Biochem. Biophys.* (*IJBBB*), 15(2):115–121 (Apr., 1978) "Studies on Lipopolysaccharide & Prostaglandin $E_1$–induced Hyperthermia on Rabbits: Part II—Biochemical Changes in Kidney".

Sethi et al., *Arch Virol* (*ARVID*), 59(3):157–172 (1979) "In vitro Acquisition of Resistance Against Herpes Simplex Virus by Permissive Murine Macrophages".

Sevier et al., *Clin. Chem.*, 27/11:1797–1806 (1981) "Monoclonal Antibodies in Clinical Immunology".

Shaw et al., *Cell Immunol.* (*CLIMB*), 41(1):122–133 (1978) "Human Lymphocyte, Monocyte, and Neutrophil Antibody–Dependent Cell–Mediated Cytotoxicity toward Human Erythrocytes".

Sheehan et al., *J. Immunol.*, 142(1):3884–3893 (Jun. 1, 1989) "Generation And Characterization of Hamster Monoclonal Antibodies that Neutralize Murine Tumor Necrosis Factor".

Shim et al., *Korean J. Biochem.*, 11(1):1–10 (1979) "The Nature of Endotoxin–induced Tumor Necrosis Factor".

Spitalny et al., *J. Exp. Med.*, 159:1560–1565 (May 1984) "Monoclonal Antibody To Murine Gamma Interferon Inhibits Lymphokine–Induced Antiviral and Macrophage Tumoricidal Activities".

Skarnes et al., *J. Exp. Med* (*JEMEA*), 154(4):1212–1224 (Oct., 1981) "Role Of Prostaglandin E In The Biphasic Fever Response To Endotoxin".

Splawinski, *Folia Med. Cracov.* (*FMCRA*), 20(2):171–190 (1978) "The Role of Prostaglandins In Fever Induced In Rats By Endotoxin" (Abstract in English p. 188).

Spooner et al., *J. Biol. Chem.*, 254:1305–1311 (Feb. 25, 1979) "Development of Lipoprotein Lipase Activity and Accumulation of Triacylglycerol in Differentiating 3T3–L1 Adipocytes".

Spooner et al., *J. Biol. Chem.*, 254:10021–10029 (1979) "Insulin Regulation of Lipoprotein Lipase Activity and Release in 3T3–L1 Adipocytes".

Springer et al., *Eur. J. Immunol*, 8:539–551 (1978) "Monoclonal xenogeneic antibodies to murine cell surface antigens:identification of novel leukocyte differentiation antigens".

Student et al., *J. Biol. Chem.*, 255:4745–4750 (May 25, 1980) "Induction of Fatty Acid Synthetase Synthesis in Differentiating 3T3–L1 Preadipocytes".

Sullivan et al., *Internat'l.* Journal of Obesity, 8, Suppl 1:241–148 (1984) "Pharmacological Modulation of Lipid Metabolism for the Treatment of Obesity".

Sultzer, *Nature*, 219:1253–1254 (Sep. 21, 1968) "Genetic Control of Leukocyte Responses to Endotoxin".

Taskinen et al., *Diabetologia*, 17:351–356 (1979) "Lipoprotein Lipase Activity of Adipose Tissue and Skeletal Muscle in Insulin–Deficient Human Diabetes".

Text Book of Biochem. with Clinical Correlations 2nd Edition (1986) John Wiley & Sons, Inc., NY, Thomas M. Devlin, Ph.D. ed. p. 374–386 "Carbohydrate Metabolism II: Special Patheways".

Tono–oka et al., Immunology, 39:607 (1980) "Human monocyte–derived chemotactic factor for granulocytes".

Torti et al., *Science*, 229:867–669 (Aug. 30, 1985) "A Macrophage Factor Inhibits Adipocyte Gene Expression: An in Vitro Model of Cachexia".

Tracey, *Tumor Necrosis Factors: The Molecules and Their Emerging Role in Medicine*, Beutler (ed.) Raven Press, NY, pp. 255–273 (1992) "The Acute and Chronic Pathophysiologic Effect so TNF: Mediation of Septic Shock and Wasting (Cachexia)".

Tracey et al., *Nature*, 330(6149):662–664 (Dec. 17, 1987) "Anti–Cachectin/TNF monoclonal antibodies prevent septic shock during lethal bacteraemia".

Verhoef et al., *J. Antimicrobiol Chemotherapy*, 38:167–182 (1996) "Issues in the adjunct therapy of severe sepsis".

Waldmann et al., *Science*, 252:1657–1662 (Jun., 1991) "Monoclonal antibodies in diagnosis and therapy".

Wannemacher, Jr. et al., *Infect. Immun.* (*INFIB*), 11(4):873–875 (Apr., 1975) "Detection of a Leukocytic Endogenous Mediator–Like Mediator of Serum Amino Acid and Zinc Depression During Various Infectious Illnesses".

Wardley et al., *Res. J. Reticuloendothel. Soc. (RESJA)*, 19(5):323–332 (May, 1976) "Antibody Dependent Cytotoxicity Mediated by Neutrophils:A possible Mechanism of Antiviral Defense".

Wecker et al., *Ann. N.Y. Acad. Sci (ANYAA)*, 249:258–263 (1975) "A T–Cell–Produced Mediator Substance Active In The Humoral Immune Response".

Werner, *Clin. Chem. Acta.*, 25:299 (1969) "Serum Protein Changes During The Acute Phase Reaction".

Westphal, et al., "Method In Carbohydrate Chemistry," eds. Whistler et al., Academic, New York, vol. 5, pp. 83–91 (1965) "Bacterial Lipopolysaccharides—'Extraction with Phenol–water and Further Applications of the Procedures'".

Wherry et al., 3rd ICAAC, Oct. 17–20, 1993:p.246 #696 "Monoclonal Antibody to Human Tumor Necrosis Factor (TNF MAb):Multi–center Efficacy and Safety Study in Patients with the Sepsis Syndrome".

Wisdom, *Clin. Chem.*, 22/8:1242–1255 (1976) "Enzyme–Immunoassay".

Wise et al., *Cell*, 13:233–242 (Feb., 1978) "Studies of Lipoprotein Lipase during the Adipose Conversion of 3T3 Cells".

Yang et al., 6th Annual Meeting of the Federation of American Societies For Experimental Biology, Atlanta, GA USA, Apr. 12–17, 1981, *Fed. Proc. (FEPRA)*, 40(3 Part 2):901 (1981) "Stress Induced Changes in Protein Metabolism: The Effect Of Leukocyte Endogenous Mediator (LEM) In The Rat".

Yelton et al., Lymphocyte Hybridomas, eds. Melcher et al., Springer–Verlag, p. 1–7 (1979) "Fusion of Mouse Myeloma and Spleen Cells".

Yelton et al., Am. Scientist, 68(5):510–516 (Sep.–Oct. 1980) "Monoclonal Antibodies—'Antibody–forming hybrids–or hybridomas–have made it possible to produce virtually unlimited supplies of a Wide variety of antibodies'".

Zubler et al., *Fed. Proc. (FEPRA)*, 38(3 part 1):1276 (1979) "Antigen–Specific Soluble Mediator Of Feedback Suppression".

* cited by examiner

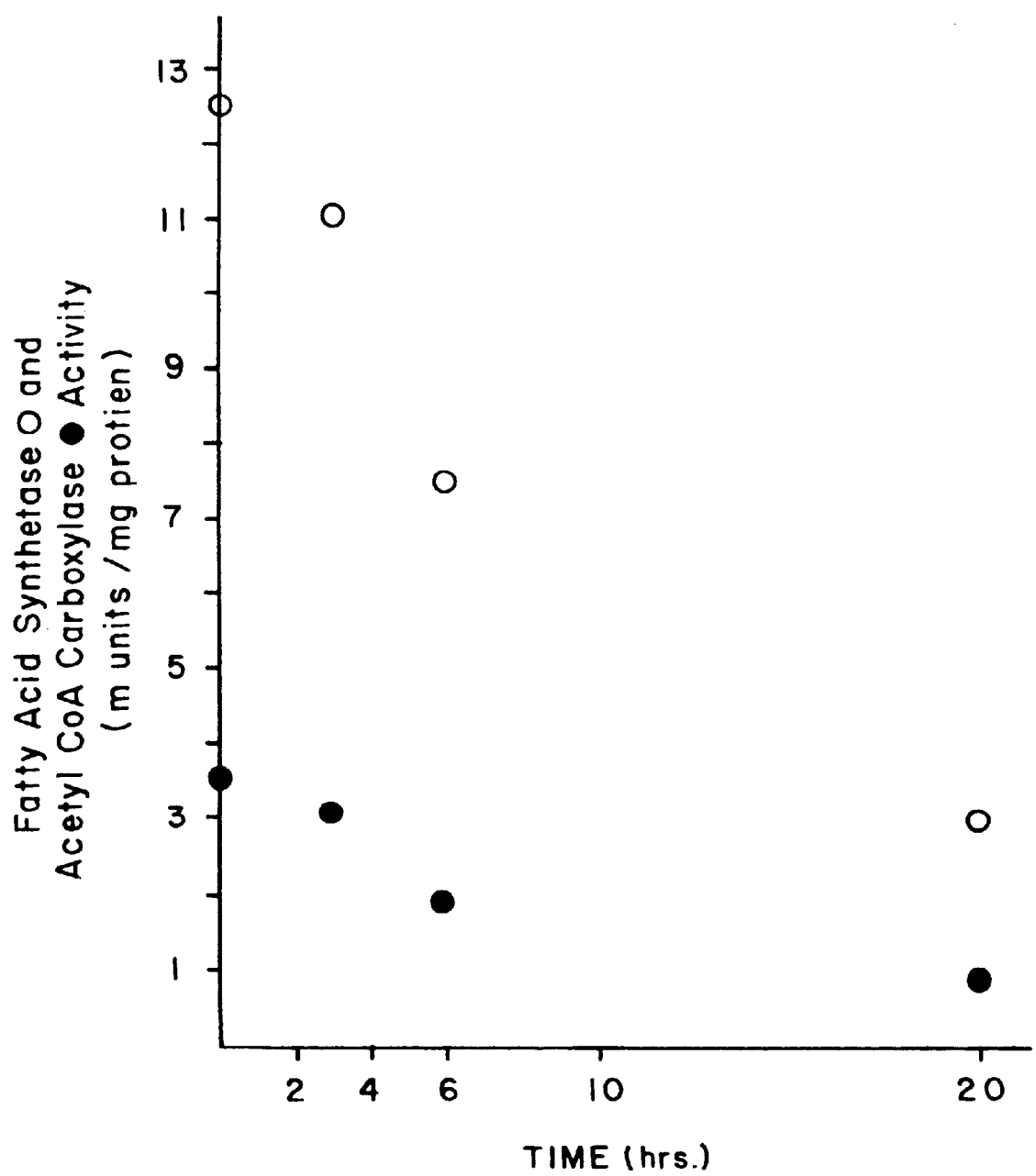
FIG. 4: Effect of conditioned medium from endoxin-treated mouse peritoneal exudate cells on the activities of acetyl CoA carboxylase and fatty acid synthetase in 3T3-L1 cells.

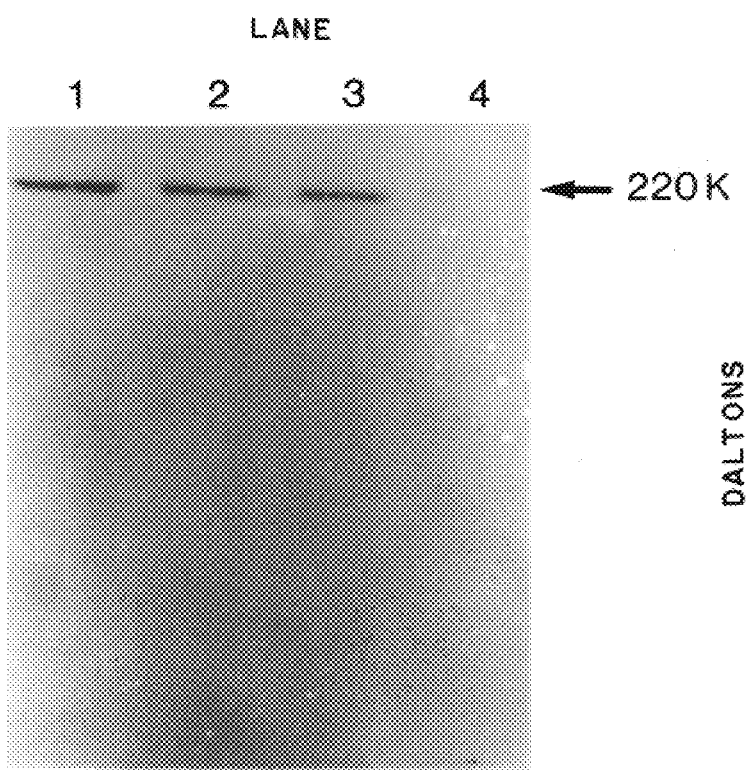
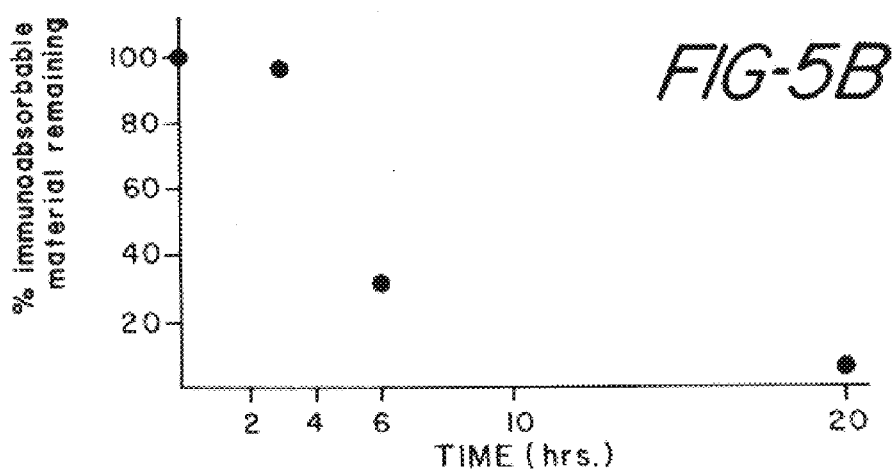
FIG. 5A & 5B: Effect of mediator that suppresses the synthesis of fatty acid synthetase.

FIG. 6A & 6B: Effect of mediator that suppresses the synthesis of acetyl CoA carboxylase.

FIG. 8: Effect of mediator on protein synthesis in the cystosolic fraction of the cells.

FIG.9: Effect of mediator on protein synthesis in the membrane fraction of the cells.

METHOD FOR REDUCING ADVERSE EFFECTS OF A HUMAN 70KDA MEDIATOR WHICH RESULTS FROM ENDOTOXIN STIMULATION OF MACROPHAGES

RELATED APPLICATIONS

This application is a Continuation of application Ser. No. 07/912,344, filed Jul. 13, 1992, now abandoned; which is a Continuation of application Ser. No. 07/283,561, filed Jul. 15, 1988, now abandoned; which is a Division of application Ser. No. 06/792,372, filed Oct. 29, 1985, now U.S. Pat. No. 4,822,776; which is a Division of application Ser. No. 06/414,098, filed Sep. 7, 1982 (now U.S. Pat. No. 4,603,106); which is a Continuation-in-Part of application Ser. No. 06/351,290, filed Feb. 22, 1982, now abandoned; which is a Continuation-in-Part of application Ser. No. 06/299,932, filed Sep. 8, 1981, now abandoned; to which Applicants claim the benefit of the filing date under 35 U.S.C. § 120.).

RELATED PUBLICATIONS

The applicants are authors or coauthors of two articles directed to the subject matter of the instant invention: (1) [applicants only] "Studies of Endotoxin-Induced Decrease in Lipoprotein Lipase Activity", J. EXP. MED. 154 at 631–639 (September, 1981, published after Sep. 8, 1981), incorporated herein by reference; and (2) [co-authors with Phillip H. Pekala and M. Daniel Lane]: "Lipoprotein Lipase Suppression in 3T3-L1 Cells by an Endotoxin-Induced Mediator from Exudate Cells", PROC. NAT'L. ACAD. SCI. 79 at 912–916 (February, 1982, published after Feb. 22, 1982), also incorporated herein by reference.

BACKGROUND OF THE INVENTION

1. Field of the Invention

The present invention is directed generally to methods and associated materials for analysis of the effect and operation of invasive stimuli upon animal hosts, and in particular, is concerned with the mechanism and magnitude of the effect that such invasive stimuli may exert upon the activity of anabolic enzymes present in the host.

2. Description of the Prior Art

Several common physiological and biochemical derangement have been seen in various mammalian hosts responding to variety of invasive stimuli such as bacterial, viral and protozoan infections, as well as tumors and endotoxemia. For example, these responses include fever, leukocytosis, hyperlipidemia, reduced food intake and activity, and other modifications in muscle, white blood cell and liver metabolism. Recently, a hypertriglyceridemia in rabbits infected with a protozoan parasite, *Trypanosoma brucei* was reported by C. A. Rouser and A. Cerami, MOL. BIOCHEM. PARASITOL. 1 at 31–38 (1980). The reported hypertriglyceridemia was accompanied by a marked decrease in the activity of the enzyme lipoprotein lipase (LPL) in peripheral tissues.

LPL activity has been observed by others, and it has been noted that this condition has existed when the human bodywas in shock. See E. B. Man, et al, "The Lipids of Serum and Liver in Patients with Hepatic Diseases", J. CLIN. INVEST. 24 at 623, et seq. (1945); See also John I. Gallin, et al, "Serum Lipids in Infection", N.ENGL. J. MED. 281 at 1081–1086 (Nov. 13, 1969); D. Farstchi, et al., "Effects of Three Bacterial Infections on Serum Lipids of Rabbits", J. BACTERIOL. 95 at 1615, et seq. (1968) S. E. Grossberg, et al., "Hyperlipaemia Following Viral Infection in the Chicken Embryo: A New Syndrome", NATURE (London) 208 at 954, et seq. (1965); Robert L. Hirsch, et al., "Hyperlipidemia, Fatty Liver and Bromsulfophthalein Retention in Rabbits Injected Intravenously with Bacterial Endotoxin", J. LIPID. RES. 5 at 563–568 (1964); and Osamu Sakaguchi, et al., "Alterations of Lipid Metabolism in Mice Injected with Endotoxins", MICROBIOL. IMMUNOL. 23 (2) at 71–85 (1979); R. F. Kampschmidt, "The Activity of Partially Purified Leukocytic Endogeneous Meliator in Endotoxin-Resistant C3H/HeJ Mice", J. LAB. CLIN. MED. 95 at 616, et seq. (1980); and Ralph F. Kampschmidt, "Leukocytic Endogeneous Mediator", J. RET. SOC. 23 (4) at 287–297 (1978).

While the existence of "mediators" was at least suspected, the effect, if any, that they had on general anabolic activity of energy storage cells was not known. The presentapplicants suspected that these "mediators" exerted a depressive effect upon the activity of certain anabolic enzymes, whose reduced activity was observed in instances where the host entered the condition of shock in response to invasion. Thus, the relationship of the mediator produced by endotoxin-stimulated peritoneal mouse exudate cells, upon endotoxin-sensitive and endotoxin insensitive mice alike, and the development through this investigation, of a reagent for measuring anabolic enzyme activity, was set forth in Ser. No. 299,932, and the further investigation of this system in conjunction with the 3T3 L1 "preadipocyte" model system, and the corresponding development of methods and associated materials for developing antibodies to the "mediators" as well as screening procedures for the identification and development of drugs capable of controlling the activity of these "mediators" was set forth in application Ser. No. 351,290. The work done to date indicates that a need exists for methodology andassociated diagnostic materials, to enable further investigationof the "mediator" phenomenon to proceed, as well as to provide practical diagnostic tools useful in the treatment of the adversesequclae of infection and concomitant shock.

SUMMARY OF THE INVENTION

In accordance with a first aspect of the present invention, a method for preparing a mediator substance for use in assessing the state of anabolic enzymes in mammals, is disclosed, whichfinds particular utility in the instance where the mammals areundergoing invasive stimuli such as, viral agents, bacteria, protozoa, tumors, endotoxemia and others. In its simplest aspect, the method comprises gathering a sample of macrophage cells from amammal and incubating a portion of the macrophage cells with astimulator material associated with an invasive event. Forexample, the stimulator material may be endotoxin, in the instanceof endotoxemia, trypanosomes, in the instance of the above mentioned protozoan parasite *Trypanosoma brucei*, and others.

While the peritoneal exudate cells illustrated in our present and previous applications exemplify sources for themacrophage cells, it is to be understood that such cells may begathered from other than the peritoneal area, and that the present invention contemplates such variation within its scope.

The macrophage cells and the stimulator material are incubated as indicated, and thereafter, the macrophage cells are induced to produce a mediator substance capable of supressing theactivity of the anabolic enzymes. Preferably, the inducement ofmediator production is accomplished during the incubation periodwhich may, for example, extend up to about 20 hours. The resulting medium may be appropriately treated to recover the mediator substance, and, for example, may be centrifuged, and the supernatant containing the mediator substance drawn off, or the mediator may be precipitated with a 40–60% solution of ammonium sulfate As mentioned earlier, the mediator substance has a broad range of effects, including inhibitive effects that have beenobserved with respect to anabolic enzymes such as lipoproteinlipase (LPL), acetyl Coenzyme A carboxylase, fatty acid synthetase and the like. Also inhibitive effects have been found with red blood cell formation, as the mediator substance has been found tobe capable of inhibiting the growth and differentiation of erythroid committed cells, by the suppression of a number of growth and differentiation inducers, such as dimethylsulfoxide (DMSO), hexamethylene bisacetamide, butyric acid, hypoxanthine and thelike, as illustrated later on herein in specific examples.

A further embodiment of the present invention comprises a method for detecting various invasive stimuli by their capability of inhibiting the activity of one or more anabolic enzymes. In this method, a plurality of macrophage cell samples, may beprepared and selectively inoculated with a number of known stimulator materials, each characteristic in its effect upon differing anabolic factors. One of the macrophage samples may be inoculated with material from the presumed situs of the infective stimulus, and all samples may thereafter be incubated in accordance with the method described above. Thereafter, testing of each of the supernatants with the mediator substances derived fromthe known stimulator materials, would provide a comparative continuum for the identification of any invasive stimulus foundpresent. This testing method may utilize the 3T3 L1 cell system, for example, in the instance where lipoprotein lipase (LPL)activity is utilized as a parameter. Likewise, in the instancewhere red cell inducers are utilized, the Friend virus-transformed erythroleukemia cells may be inoculated and thereafter observed.See Friend, C., Sher, W. Holland J. G. and Sato, G. PROC. NATL.ACAD. SCI. 68, at 378–382; Marks, P. A., Rifkind, R. A., Terada, M., Ruben, R. C., Gazitt, Y. and Fibach, E. in ICN-UCLA Symposia on Molecular and Cellular Biology, Vol. X. "Hematopoietic Cell Differentiation". Ed. by D. W. Golde, M. J. Kline, D. Metcalf and C. F. Fox (Academi Press, New York), pp. 25–35 (1978). Naturally, other cellular systems may be utilized in the instance wherespecific activities may be appropriately observed, and the invention is not limited to the specific cellular systems set forth herein.

The invention includes methods for detecting the presence of samples of the various invasive stimuli in mammals by measuring mediator substance activity in the mammals. Thus, a number of mediatorsubstances may be prepared from the incubation of individual cell samples with known stimulator materials, and these mediator samples may thereafter be used to raise antibodies capable of specifically detecting the presence of the respective mediator substance. These antibodies may be prepared by known techniques, includingthe well known hybridoma technique for example, with fused mousespleen lymphocytes and myeloma, or by development in various animals such as rabbits, goats and other mammals. The known mediator samples and their antibodies may be appropriately labelled and utilized to test for the presence of the mediator substance in, for example, serum, as one may measure the degree of infection, and determine whether infection is increasing or abating, by observing the activity of the mediator substance therein. A variety of well known immunological techniques may be utilized in accordance with this aspect of the present invention, including single and double antibody techniques, utilizing detectible labels associated with either the known mediator substances, or their respective associated antibodies.

A further embodiment of the present invention relates to a method for preventing the occurrence of shock in mammals,comprising detecting the presence and shock promoting activity ofa mediator substance in the mammal, and thereafter administeringan antibody to the mediator substance, in an amount effective toprevent the development of shock in the mammal.

The invention particularly relates to a method of treating shock in humans, comprising administering to a human a shock-reducing amount of an antibody specific to a mediator substance.

Also, an assay system is disclosed and may be prepared for the screening of drugs potentially effective to inhibit thesynthesis or activity of the mediator substance. In the former instance, the effect of the test drug on the production of mediator by stimulated macrophages is determined, In the latter instance,a mediator substance may be introduced to cellular test systems, such as the 3T3 L1 cells, and the prospective drug may then be introduced to the resulting cell culture and the culture thereafter examined to observe any changes in mediator activity, either fromthe addition of the prospective drug alone, or the effect ofadded quantities of the known mediator substance.

A number of materials, compounds and agents have already been tested to determine their effect if any on mediator substanceproduction and activity. As discussed in further detail in thedescription, infra., only the steroid dexamethasone exhibited any inhibitory effect, and that effect appeared to be limited to theproduction of the mediator substance. Further agents, drugs, etc. can however be tested in the manner such as that employed withdexamethasone, and described herein.

The preparation of the mediator substance, and the determination of the importance of its activity, has resulted in the development of numerous avenues of diagnostic and therapeutic application. It is clear from the foregoing and following, thatthe detection of invasive stimuli may be made by the identification of the mediator substance, either directly or through the development of antibodies useful in immunological diagnosis.Further, these same antibodies may be utilized for direct treatment by control of mediator activity, to avert the development of shock in mammals, while the mediator substance may be utilized as screening agents in an assay system for the identification ofdrugs, agents and other substance (capable of neutralizing theadverse effects of the mediator substance, and thereby providing treatment of the adverse sequelae of infection.

Accordingly, it is a principal object of the present invention to provide a method for the preparation of a mediator substance exhibiting suppressive effects upon anabolic enzyme activity in mammals.

It is a further object of the present invention to provide a method for detecting the presence of a mediator substance in mammals in which invasive stimuli such as infection are suspected to be present.

It is a further object of the present invention to provide a method and associated assay system, for screening substance such as drugs, agents and the like, potentially effective incombating the adverse effects of the mediator substances in mammals.

It is a yet further object of the present invention to provide a method for the treatment of mammals to control the activity of said mediator substance so as to mitigate or avert the adverse consequences of their activity.

Other objects and advantages will become apparent to those skilled in the art from a review of the ensuing description, which proceeds with reference to the following illustrative drawings

DESCRIPTION OF THE DRAWINGS

FIG. 4 shows the effect of conditioned medium from endotoxin-treated mouse peritoneal exudate cells on the activities of acetyl CoA carboxylase and fatty acid synthetase in 3T3-L1 cells. Three hundred (300) µl of conditioned medium was added to cultures of 3T3-L1 cells ($4.2 \times 10^6$ cells/dish) in 6 cm dishes containing 3.5 ml of DMIE medium and 10% fetal calf serum. After the indicated times of incubation, the enzymatic activity of acetyl CoA carboxylase (identified by the symbol "•") and fatty acid synthetase (identified by the symbol "○") on a digitonin releaseable cytosolic fraction of the cells was assessed.

FIGS. 5A and 5B show the effect of mediator that suppresses the synthesis of acetyl CoA-carboxylase. At the indicated times after exposure of the 3T3-L1 cells to the mediator (300 µl of conditioned medium, the cells were pulse-labeled with 0.5 mCi of $^{35}$S-methionine for 1 hour. Cytosolic fractions were obtained by digitonin treatment of a monolayer. Aliquots of the cytosolic fractions ($2 \times 10^5$ cpm for all determinations) were incubated with anti-acetyl CoA carboxylase and the immunoprecipitable material isolated and characterized as described in Example II, infra. Panel A: Autoradiogram of a 7.5%-acrylamide-0.1% SDS gel analysis of immunoadsorbable protein. Lane 1—control, without exposure to mediator; Lanes 2, 3, and 4—exposure of the cells to the mediator for 3, 6 and 20 hours, respectively. Panel B: Results of a densitometric scan of the autoradiogram, indicating percent of immunoadsorbable material remaining relative to control, after exposure to the mediator.

Friend cells (clone DS-19) were incubated for 96 hours in the absence or in the presence of $Me_2SO$ (1.5 vol %). Conditioned media (80 µl/ml of growth medium) from mouse peritoneal macrophage cultures stimulated or not stimulated with endotoxin(5 µg/ml) were added at the beginning of culture. Cell members were counted with a Cytograf model 6300 and expressed as per cent inhibition of the control cells. Cell number in untreated control culture was $3 \times 10^6$ cells/ml. Heme content was determined fluorometrically as described previously (Sassa, S., Granick, S., Chang, C. and Kappas, A. (1975) In Erythropoiesis, ed. by K. Nakao, J. W. Fisher and F. Takaku (University of Tokyo Press, Tokyo) pp. 383–396). Data are the mean of duplicate determinations. The number of trypan blue positive cells assessed by Cytograf counting was 8–10% for all cultures.

FIGS. 11A and 11B show the dose dependent effect of the endotoxin-stimulated macrophage mediator on cell growth and erythroid differentiation of $Me_2SO$-treated Friend cells. Cells were incubated for 96 hours in the presence of 1.5% $Me_2SO$ with increasing concentrations of the macrophage mediator. Assays of enzymes and intermediates were performed as described in Example III, infra. Data are the mean of duplicate determinations.

Figure 12:
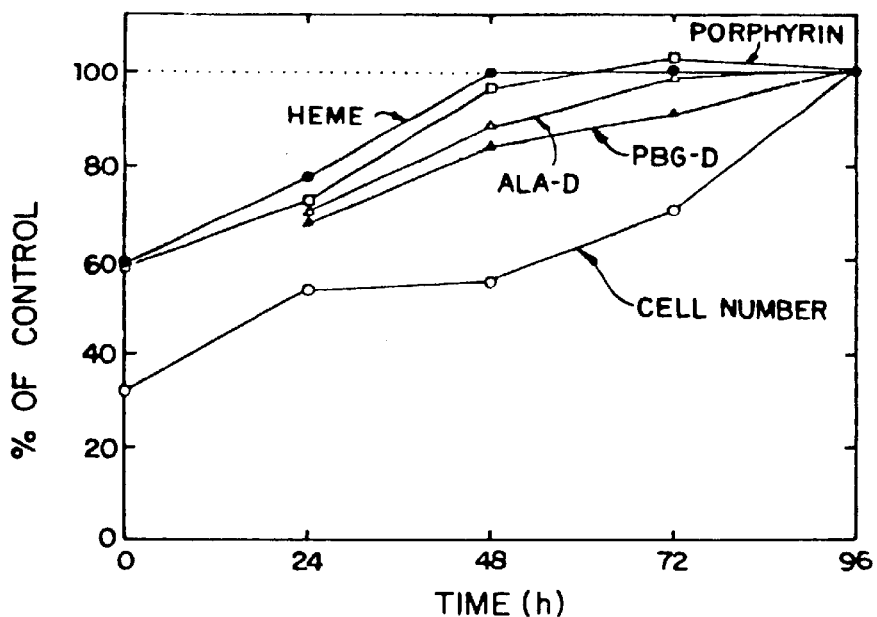

FIG. 12 shows the effect of delayed addition of the endotoxin-stimulated macrophage mediator on cell growth anderythroid differentiation.

Friend cells were incubated for 96 hours without changing the medium. $Me_2SO$ was added at time 0 to a final concentration of 1.5 vol %, while the endotoxin-stimulated macrophage mediator was added at the times indicated on theabscissa (80 μl conditioned medium per ml of growth medium). Cell number, activities of ALA dehydratase and PBG deaminase, hemeand protoporphyrin contents were assayed at the end of incubationas described in Example III, infra. Data are the mean of duplicatedeterminations.

Values for control cultures treated with Me SO alone were as follows:

| | |
|---|---|
| Cell number | 3.0 ($\times 10^{-6}$/ml) |
| ALA dehydratase | 3.00 (nmol PBG/$10^6$ cells, h) |
| PBG deaminase | 120 (pmol uroporphyrinogen/$10^6$ cells, h) |
| Protoporphyrin | 0.57 (pmol/$10^6$ cells) |
| Heme | 520 (pmol/$10^6$ cells) |

FIGS. 13A and 13B show the effect of the endotoxin-stimulated macrophage mediator on cell growth and heme content in Friendcells treated with HMBA, butyric acid, hypoxanthine or hemin.

Cells were incubated for 96 hours without changing the medium; inducing chemicals and the endotoxin-stimulated macrophage mediator (80 1 added/ml of growth medium) time 0. Final concentrations of chemicals were mM for HMBA, 1.3 mM for butyric acid, bmM for hypoxanthine and 0.1 mM for hemin. Assays were performed as described in Example III, infra. Data are the mean of duplicate determinations.

FIGS. 14A and 14B show the effect of endotoxin-stimulated macrophage mediator on the growth and differentiation of Friend cells growing at a constant rate.

DETAILED DESCRIPTION

As disclosed in our above referenced co-pending applications on this subject matter, we have discovered an agent which we identify herein as a mediator substance, that is produced bymammalian cells in response to stimulation by materials we referto herein as stimulator materials, that characteristically accompany an invasive stimulus, such as bacteria, virus, some tumors, protozoa and other toxins such as endotoxemia. We have observedthat the mediator substance causes the metabolism of certain of the cells of the mammal to switch from an anabolic state to acatabolic state. In particular, the mediator substance appears to suppress the activity of anabolic enzymes, such as lipoproteinlipase (LPL), and the other enzymes and inducing agents listedearlier herein. It is theorized that this mediator substance is part of a communications system in mammals, between the immune system and the energy storage tissues of the body. Thus, inresponse to various invasive stimuli in mammals, such as thoselisted before, it is theorized that the mediator substance is produced and exert an effect on energy storage tissue such asadipose tissue, muscle, the liver,and the like, of the impendingneed for energy to combat the invasion. More particularly, themediator substance may cause these storage tissues to switch from an anabolic to a catabolic state, to facilitate the supplyof such energy. If the invasion is of short duration, themammal can quickly recover and replenish its energy stores; however, if the invasion is of a chronic nature, shock generally manifested by complete energy depletion, cachexia and death, can result.

During the initial work wherein the foregoing observations were made, the method for preparing the mediator was developed, and an illustrative preparation is set forth initially in Example I, in paragraph D, wherein peritoneal exudate cells were appropriately cultured and thereafter incubated in the presence of the known stimulator material endotoxin. After incubation, the macrophage cells are induced to produce the mediator substance. In one aspect, such inducement can occur over anextended incubation, i.e. on the order of 20 hours or more. The exact period for such incubation, however, may vary, and theinvention is not limited to a specific time period.

Thereafter, the mediator substance may be recovered from the cell culture and stored for later use in one or more of theways disclosed herein. Recovery may be effected by one of numerous well known techniques, including centrifugation and precipitation. For example, the culture described in paragraph D of Example I, was centrifuged and the supernatant thereafter drawnoff. Alternately, the mediator may be precipitated either witha 40–60% solution of ammonium sulfate or by adsorption onto DEAE cellulose or like exchange resins. The choice of the particularmethod for recovery of the mediator substance is within the skillof the art.

The invention also relates to methods for detecting the presence of invasive stimuli in mammalian hosts by measuring thepresence and activity of the mediator substance. As mentioned earlier, the mediator substance can be used to produce antibodies to themselves in rabbits, goats, sheep, chickens or other mammals, by a variety of known techniques, including thehybridoma technique utilizing, for example, fused mouse spleenlymphocytes and myeloma cells. The antibody can be isolated bystandard techniques and utilized as a test for the presence ofthe mediator substance in the suspected mammalian hosts.

Further, the antibody or antibodies can be utilized in another species as though they were antigens, to raise further antibodies. Both types of antibodies can be used to determinethe presence of mediator substance activity in the mammalianbody, particularly in human serum, so as to determine the presenceof invasive stimuli such as bacterial, viral, or protozoan infection, or the presence of certain tumors, and to follow the course of the disease. For purposes of the following explanation, theantibody or antibodies to mediator activity, will be referred toas $Ab_1$ the antibody or antibodies raised in another species will be identified as $Ab_2$.

The presence of mediator substance activity(ies) in the serum of patients suspected of harboring toxic levels thereof canbe ascertained by the usual immunological procedures applicable tosuch determinations. A number of useful procedures are known.Three such procedures which are especially useful utilize eithermediator labeled with a detectable label, antibody $Ab_1$ labeled with a detectable label, or antibody $Ab_2$ labeled with a detectable label. The procedures may be summarized by the following equations wherein the asterisk indicates that the particle is labeled, and "Med" stands for mediator activity:

A. $Med^* + Ab_1 = Med^* Ab_1$
B. $Med + Ab_1^* = Med Ab_1^*$
C. $Med + Ab_1 + Ab_2^* = Med\ Ab_1 Ab_2^*$

The procedures and their application are all familiar to those skilled in the art and accordingly may be utilized interchangeably within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody", or "DASP" procedure.

In each instance the mediator substance forms a complex with one or more antibody(ies) and that one member of the complexis labeled with a detectable label. The fact that a complex hasformed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_1$ may be raised in rabbits using a mediator as the antigen and $Ab_2$ may be raised in goats using $Ab_1$ as an antigen. $Ab_2$ therefore would be an anti-rabbit antibody raised in goats. For purposes of thisdescription and claims, $Ab_1$ will be referred to as a mediator activity antibody and $Ab_2$ will be referred to as an antibody reactive with a mediator activity antibody or, in the alternative, an "anti-antibody".

The labels most commonly employed for these studies are radioactive elements, enzymes, chemicals which fluoresce whenexposed to ultraviolet light, and others.

A number of fluorescent materials are known and can be utilized as labels. These include, for example fluorescein, rhodamine and auramine. A preferred detecting material is anti-rabbit antibody prepared in goats and conjugated with fluorescein throughan isothiocyanate.

The mediator composition(s) can also be labeled with a radioactive element or with an enzyme. The radioactive label canbe detected by any of the currently available counting procedures. The preferred isotope $^{14}C$, $^{131}I$, $^{3}H$, $^{125}I$ and $^{35}S$. The enzyme label can be detected by any of the presently utilized calorimetric spectrophotometric, fluorospectrophotometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, $\beta$-glucuronidase, $\beta$-D-glucosidase, $\beta$-D-galactosidase, urease, glucose oxidase plus peroxidase, galactose oxidase plus peroxidase and acid phosphatase. U.S. Pat. Nos. 3,654,090; 3,850,752; 4,016,043; are referred to by way of example for their disclosure of alternate labeling material, and materialsHigh levels of mediator activity in the mammalian bodymay be toxic to the mammal and cause irreversible shock. Theantibody(ies) specific to a mediator is useful to treat hosts suffering from this metabolic derangement. The patient can be treated for example, parenterally, with a shock-reducing, effective doseof the antibody to neutralize at least a portion of the mediator.The dose will, of course, vary in accordance with the factors wellknown and understood by the physician or veterinarian such as age,weight, general health of the patient and the concentration of themediator.

In a further embodiment of this invention, commercial test kits suitable for use by a medical specialist may be prepared to determine the presence or absence of mediator substances in a suspected host. In accordance with the testing techniquesdiscussed above, one class of such kits will contain at least thelabeled mediator or its binding partner, an antibody specificthereto. Another which contain at least $Ab_1$ together with labeled $Ab_2$. Still another will contain at least $Ab_1$ and directions, of course, depending upon the method selected, e.g., "competitive", "sandwich", "DASP" and the like. The kits may also contain peripheral reagents such as buffers, stabilizers, etc.

Accordingly, test kits may be prepared with various components to detect the mediator substance in sera or aqueous media. A first kit may be prepared to comprise:

(a) a predetermined amount of at least one labeled immuno-chemically reactive component obtained by the direct or indirect attachment of a mediator substance or a specific binding partner thereto to a detectable label;

(b) other reagents; and (c) directions for use of said kit.

More specifically, a diagnostic test kit for the demonstration of a mammal's reaction to invasive stimuli may be prepared comprising (a) a known amount of one mediator substance as described above (or its binding partner) generally bound to a solid phase to form a immunosorbent, or in the alternative, bound to a suitable tag;

(b) if necessary, other reagents; and (c) directions for use of said test kit.

Additional kits may be formulated to take advantage of numerous extant immunological protocols and techniques, and suchmodifications are considered within the scope of the invention.

In yet another aspect of the invention, antibodies specific to the aforementioned mediator may be administered in pharmaceutical compositions in response to shock produced by viruses, bacteria, protozoa, etc. These pharmaceutical compositions comprise:

(a) a pharmaceutically effective amount of the antibody together with (b) a pharmaceutically acceptable carrier. With the aid of suitable liquids, the antibodies may be used ininjection preparations in the form of solutions. These compositions may then be administered to a human in the above manner in shock-reducing amounts to dissipate, if not overcome, the effectsof the invasion/shock.

As an adjunct to the development of antibodies and their use in the techniques described above, the present invention extends to methods of treatment of various conditions, such as shock etc., that are found to exist as a result of undesirably high mediator substance activity in the mammalian host. In such instance, the method of treatment may include the detection of the presence and activity of the particular mediator substance, andthe subsequent administration of the appropriate antibody or antibodies to the host, in amounts effective to neutralize the undesired mediator substance activity.

Conversely, certain adverse conditions in mammals such a obesity, may result from excess anabolic activity. For example, obesity may be caused by undesirably high levels of activity of the anabolic enzymes lipoprotein lipase, acetyl Coenzyme A carboxylase and fatty acid synthease. The invention accordingly includes a method for treating obesity, comprising administering a mediator substance in an acceptable form, and in an amount effective to assist in restoring proper body weight. Administration of such treatment, however, would be under strict control by a physician, and the amount, manner and frequency of administration of the mediator would be carefully determined and constantly monitored.

In addition to treatment with antibodies raised by a mediator substance, the present invention includes an assay system, for the examination of potential substances, such as drugs, agents, etc. to inhibit the synthesis or activity of a mediator substance. As described earlier appropriate cell cultures such as the 3T3-L1 and the Friend virus transformed erythroleukemia cells may be initially treated with a particular mediator to inhibit the activity of a particular anabolic actor, after which the potential drug etc. may be added, and the resulting cell culture observed to determine whether changes in the activity of the anabolic actor have taken place. Whilethe foregoing description makes reference to specific cell cultures for thepresent assay, it is to be understood that the invention is not limited thereto.

Certain compounds have already been screened, to determine whether or not each inhibited mediator production and/or the effect of the mediator. Compounds tested and the results ofsuch tests are set forth in the table, below.

TABLE

| Entity | Mediator Production | Mediator Effect |
|---|---|---|
| Dexamethasone $10^{-6}$M | + | – |
| Aspirin $10^{-3}$M | – | – |
| Indomethacin $10^{-5}$ | – | – |
| Nalaxone $10^{-5M}$ | – | – |
| Thyroid Releasing Factor $10^{-7}$M | – | – |

(+ denotes yes; – denotes no)

As can be seen, only dexamethasone seems to have any effect. And even dexamethasone only has an effect on "mediator" production and, thus, is only effective at the beginning of the process. Oncethe mediator has been produced, the dexamethasone does not seem tohave any further impact.

The following examples relate to the isolation of the mediator substance, and the observation of its activity, as related to certain anabolic enzymes etc. A review of the following should lend greater appreciation to the origins and potentials of the present invention. Naturally, however, the specific materials and techniques may vary, as explained earlier, so that the following is presented as illustrative, but not restrictive of the present invention.

It should be noted that the terms "mediator" and "mediator substance", whether used in the singular or in the plural, are intended to refer to the same material that is isolated from macrophage cells that have been incubated with a stimulator material as disclosed herein, and both singular and plural usages of these terms, where present, should be viewed as equivalent for purposes of the present disclosure. At present, the exact composition of the mediator is unknown and, therefore, also unknown is whether the mediator is a single material or a mixture. Accordingly, the present terminology is intended to cover the "mediator" whether it is a single material or a mixture of materials. The term "mediator activity composition" and its plural may be distinct, as, although the mediator or mediator substance would be the same, the remainder of the composition may possibly vary depending upon the degree to which other cellular constituents, factors, etc. may be present therein.

EXAMPLE I

Isolation of Mediator Activity Compositions

A. Mice used in Testing:

Male C3H/HeN endotoxin sensitive mice (7–10 wk: 18–25 g) were obtained from Charles River Breeding Laboratory (Wilmington, Mass.). Male C3H/HeJ, endotoxin-resistant mice (7–10 wk: 18–25 g) were obtained from The Jackson Laboratory (Bar Harbor, Me.). Mice were fed ad libitum on Rodent Laboratory Chow (Ralston Purina Co., St. Louis, Mo.) until they were utilized. The chow diet was removed 24 hours prior to each experiment and replaced with a solution of 25% sucrose in water. The animals, once injected, were only allowed access to water. Three to 10 C3H/HeN or C3H/HeJ mice were employed in each experimental group.

In conducting the various experiments, each mouse was injected intraperitoneally with one of the following: (i) 0.04 to 100 μg of endotoxin; (ii) 0.5 ml of serum obtained from C3H/HeN mice treated with endotoxin or saline; (iii) 1 ml of medium from cultures of peritoneal exudate cells of mice incubated in the presence or absence of endotoxin. Animals were sacrificed by decapitation.

B. Assay for Serum Triglyceride Concentration and Tissue Lipoprotein Lipase Activity:

The triglyceride concentration was measured with an enzymatic assay (Triglyceride Test Set No.961, Hycel Inc., Houston, Tex.). Lipoprotein lipase activity was assayed by the methods of Pykalisto, et al., PROC. SOC. EXP.BIOL. MED., 148 at 297 (1975); and Taskinen, et al., DIABETOLOGIA 17 at 351 (1979), both incorporated herein, with some modifications. Epididymal fat pads were excised immediately after the decapitation of each mouse. The tissues were rinsed in sterile Dulbecco's Modified Eagle medium (DME) (Gibco, Grand Island, N.Y.) containing 2% bovine serum albumin (fraction V, Reheis Chemical Company, Phoenix, Ariz.) and blotted on sterile filter paper. The tissues were minced with scissors, put into pre-weighed sterilepolypropylene culture tubes (17×100 mm, Falcon Division of Bector, Dickinson and Company, Cockeysville, Md.) containing 1 ml of DDME medium supplemented with 2% bovine serum albumin, and 2 U of heparin to release LPL (Lipo-Hepin, Riker Laboratories, Inc.,Northridge, Calif.). Tubes with the tissues were sealed under 5% $CO_2$, balance air and incubated at room temperature with continuous gentle shaking. Tissue weight was determined by the difference of the weights of the tube before and after the addition of the tissue. Approximately 100–300 mg of tissue was removed and the activity of lipoprotein lipase released from the tissue was determined.

The enzyme assay was carried out by the method of Nilsson-Ehle and Shotz, J. LIPID. RES. 17 at 536 (1976), incorporated herein, with minor modifications. The samples were incubated at 37° C. for 90 minutes of incubation. Each sample was assayed in duplicate. One milliunit of the enzyme activity was defined as one nanomole of free fatty acid released per minute. The enzyme activity released per gram of wet tissue was compared between experimental groups and control groups of each study since there was considerable variation of LPL activity day to day. In order tocompare the data between experiments, the data was expressed aspercent of the average activity of the control group. The rangeobserved in C3H/HeN mice was from 32 to 59 mU/g for adipose tissue Values of 31 of 172 mU/g for adipose tissue were observed in C3H/HeJ mice.

C. Collection of Serum for Endotoxin Treated Mice:

Blood was obtained under sterile conditions from the axillary pit of C3H/HeN mice 2 hours after i.p. injection of endotoxin (either 2 or 100 μg/mouse) in 0.1 ml of saline or saline alone. Serum was prepared within one hour after bleeding and either used immediately or kept at 80° C. until use.

D. Preparation of Endotoxin Treated Peritoneal Exudative Cells:

Peritoneal exudate cells were obtained by peritoneal lavage with pyrogen-free saline (Abbott Laboratories, North Chicago, Ill.) from C3H/HeN mice (25–33 g). These mice were injected imp 6 days prior to lavage with 3 ml of sterile Brewer's thioglycollate medium (Difco Laboratories, Detroit, Mich.) to increase cell production. The peritoneal exudate cells obtained by this procedure consist of approximately 60% macrophages, 20% small lymphocytes, 15% large lymphocytes, and 5% eosinophils.

The exudate cells ($2\times10^6$ cells/well) were incubated in serum-free RPMI-1640 medium (Gibco, Grand Island, N.Y.) in culture plates containing 4.5 cm² wells at 37° C. in 5% $CO_2$. After 3 hours, the cultures were washed three times with the medium to remove nonadherent cells. The cells which adhered to the dish were mainly macrophages. In the various testing procedures, the cells were incubated in serum-free RPMI-1640 medium in the presence or absence of endotoxin (10 µg/ml). The culture medium was removed at 26 hours incubation and centrifuged at 1000 g for 5 minutes at 4° C. The supernatant was used for testing immediately or kept at −80° C. until required for testing. No difference in activity was noted after storage for one month under these conditions.

The various studies and isolation procedures will now be described.

E. Mediator Activity Produced in Mice:

The LPL activity from adipose tissue and the serum triglyceride concentration of endotoxin-sensitive mice which had been injected with either saline (controls or 100 µg of endotoxin) 16 hours before sacrifice was observed. This amount of endotoxin corresponds in this strain of mice to a dose in which half the animals die within three days after injection. It was observed that the LPL activity of adipose tissue in the endotoxin-treated animals was depressed to 4.5% of the control values while the triglyceride concentration in the serum of the endotoxin treated animals were elevated 2.6 times that of control animals.

The fact that the lowering of LPL activity is to be attributed to mediator activity produced as a result of stimulation by endotoxin and not to the endotoxin itself is supported by the results obtained when the serum from endotoxin-sensitive mice which had been treated with 100 µg of endotoxin 2 hours prior to bleeding was injected into another group of endotoxin-sensitive mice. For this test, the control group was injected with serum obtained from another group of endotoxin-sensitive mice which had been injected with pyrogen-free saline. LPL activity in epididymal fat pads were measured 16 hours later.

Figure 1A:
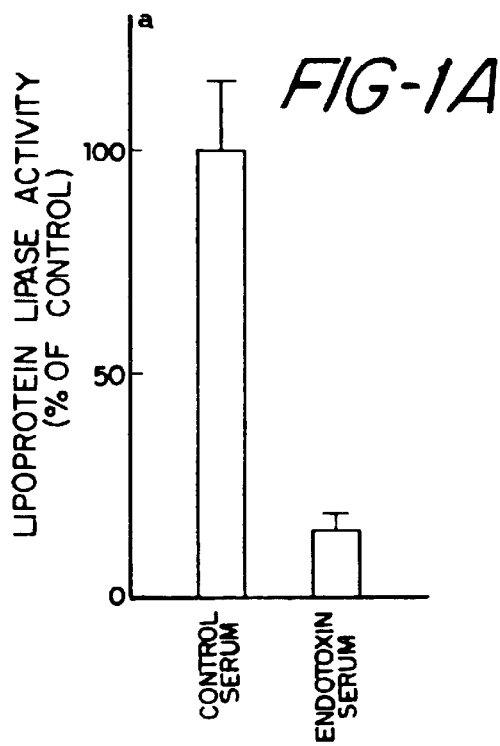
FIG. 1A shows the effect of serum from endotoxin-sensitive mice treated with endotoxin on adipose tissue LPL activity in endotoxin-sensitive mice. Mediator activity was observed and conclusions drawn as set forth in Example, paragraph E herein. The data are expressed as the mean (+SEM) of six animals for each group.

As further illustrated in FIG. 1A, the serum from endotoxin-treated mice markedly suppressed LPL activity in these animals compared to the activity in the control group of animals. Since greater than 90% of endotoxin is known to be cleared from circulation in 15 minutes, it is clear that the observed effect on LPL activity is not due to a direct effect on any remaining endotoxin present in the serum 2 hours after injection. It must be caused by a humoral factor or mediator produced as a result of the endotoxin injection.

Figure 1B:
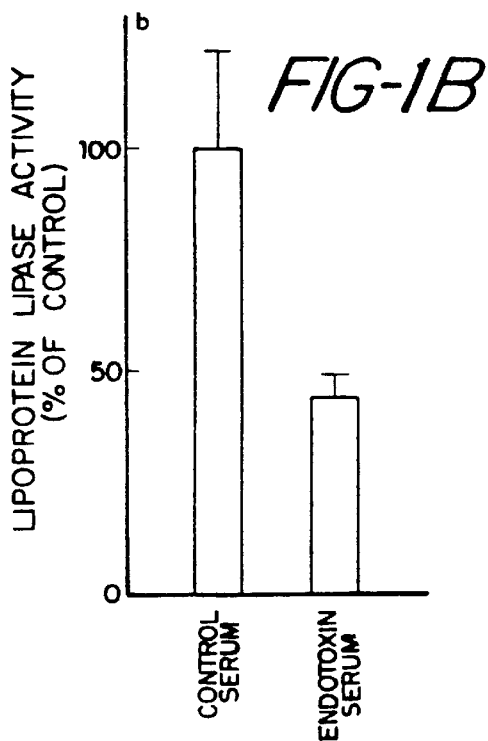
FIG. 1B shows the effect of serum from endotoxin-sensitive mice treated with endotoxin on adipose tissue LPL activity in endotoxin-resistant mice. The data are expressed as the mean (±SEM) of three animals for each group.

To further exclude direct endotoxin effects, serum obtained from the sensitive C3H/HeN strain of mice which had been injected 2 hours previously with a smaller amount (2 µg) of endotoxin was injected into endotoxin-resistant C3H/HeJ mice. The LPL activity of adipose tissue was measured 16 hours after the injection to minimize the possibility of direct endotoxin effect and revealed a 55-percent decrease of LPL activity as illustrated in FIG. 1B. Since resistant animals do not respond to this small amount of endotoxin, this observation again establishes that a humoral mediator is involved to which the resistant mice are capable of responding.

Figure 2:
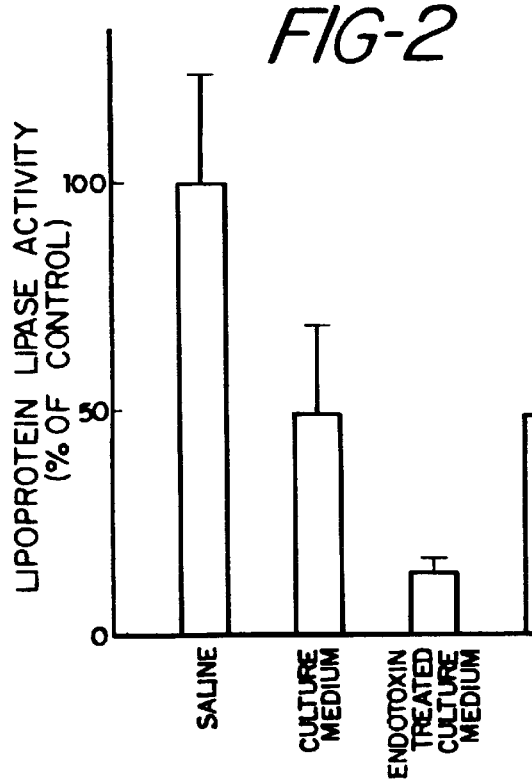
FIG. 2 shows the effect of medium from exudate cell cultures on adipose tissue LPL in endotoxin-resistant mice. The data are presented as the mean (±SEM) of four-or five animals.

F. Mediator Activity Produced in Mice Peritoneal Exudate Cells:

Experiments were undertaken to show that exudate cells could be stimulated to produce the mediator by which endotoxin suppresses the LPL activity of adipose tissue. Exudate cells were obtained from endotoxin-sensitive (C3H/HeN) mice by peritoneal lavage. These cells were incubated in vitro in the presence of 10 µg/ml or absence of endotoxin. One ml of the media from these cell cultures was injected into the endotoxin-resistant strain of C3H/HeJ mice. As displayed in FIG. 2, the average LPL activity in adipose tissue of animals injected with medium from the exudate-cells incubated with endotoxin was 32% of that of mice which received either medium from cell cultures without added endotoxin or medium containing endotoxin but without cells. The difference in enzyme activity between animals treated with medium from endotoxin treated cell cultures and those animals treated with saline alone was much greater than the other controls, suggesting that a small amount of mediator was released by exudate cells in the absence of endotoxin and that the small amount of endotoxin in the medium without cells was enough to partially lower LPL activity.

From the above, it is clear that endotoxin administration markedly suppresses adipose tissue LPL in genetic strains of mice which are sensitive to endotoxin shock and death. This action is mediated by humoral factor or factors which can suppress adipose tissue LPL in mice not sensitive to endotoxin shock, as well as in mice which are sensitive. Peritoneal exudate cells sensitive to endotoxin are also capable of producing this humoral mediator G. Isolation of Mediator Activity Compositions from Mouse Peritoneal Exudate Cells:

Culture medium is collected from mouse peritoneal exudate cells cultured in RPMI-1640 growth medium exposed to 10 µg/ml of endotoxin for 24 to 36 hours and centrifuged at 500 rpm for 10 minutes at 4° C. The supernatant is subjected to ultrafiltration through an Amicon PM-10 membrane with a 10,000-Dalton cut-off. The volume of the retentate is concentrated by filtration to approximately 7 ml, placed on a Sephacryl 300 column (1.695 cm) and eluted with phosphate-buffered saline (PBS) (pH 7.4) at 4 ml/hr and 4° C. The volume of each collected fraction was 3.6 ml. The fractions were analyzed for LPL activity. Fractions eluting at 108 to 115 ml and 133 to 140 ml were found to be active in the LPL assay. The molecular weights of the mediator active compositions in these fractions are about 300,000 and 70,000 Daltons, respectively.

The lyophylized filtrate from the ultrafiltration is dissolved in a minimal amount of distilled water, chromatographed on a Sephadex G 50 column (1.6×95 cm), and eluted with PBS (pH 7.4) at a flow rate of 6 ml/hr. Fractions of 3 ml were collected and analyzed for LPL activity. The activity was located in fractions eluting at 170 to 179 ml which corresponds to a molecular weight to about 400 to 1,000 Daltons.

The approximate molecular weights were determined in accordance with standard practice by comparison with proteins of known molecular weight. The standards employed were ferritin, molecular weight—440,000 Daltons; bovine serum albumin, molecular weight—68,000; carbonic anhydrase, molecular weight—30,000; and ribonuclease, molecular weight—17,000; all in Daltons. As is known to those skilled in the art, molecular weights determined by this procedure are accurate to about 20%.

Mediator activity compositions can also be isolated from mouse peritoneal exudate cells by vacuum dialysis using a Millexmembrane (Millipore Corporation, Bedford, Mass.) according to the following procedure.

Vacuum dialysis was carried out in dialysis tubing with molecular weight cut-offs at 13,000–14,000 Daltons. Samples of conditioned medium obtained from endotoxin-treated exudate cell cultures were placed under vacuum for 6 hours at 4° C. with a 40-percent reduction in volume. Aliquots from inside and outside the bag were assayed for mediator activity.

It was found that all of the activity was retained during vacuum dialysis with membranes having a 12,000-Dalton pore cutoff. The mediator composition isolated by this procedure, therefore, has a molecular weight greater than 12,000 Daltons. This composition contains the two higher molecular weight compositions previously described. The reason that the lowest molecular weight composition is not obtained is not clear. Possibly because it is absorbed in the Millex membrane or because the procedure with the Amicon filter is more rapid.

The stability of the various mediator compositions to heat was assessed by heating at 100° C. for 15 minutes. The inhibitory effect of the mediators on the lipoprotein lipase was completely abolished by this treatment.

To determine whether the mediators are intracellular constituents of nontreated cells, exudate cells were sonicated and the extract was assayed for mediator activity. These extracts had no measurable mediator. The mediators, therefore, are not a normal intracellular substance of exudate cells, but are synthesized or processed in these cells following stimulation by endotoxin.

The fact that the mediator activity compositions are in the tissue culture medium of tissue cultures of peritoneal exudate cells make it clear that they are water-soluble.

The mediators, therefore, are capable of reducing LPL activity in the mammalian body, can be isolated by standard procedures such as chromatography, dialysis and gel electrophoresis from the serum of endotoxin-treated animals or from a cell culture of peritoneal exudate cells incubated with endotoxin.

H. Studies of 3T3-L1 Preadipocytes:

The properties of the mediator compositions were further investigated using the well defined 3T3-L1 "preadipocyte" model system, by the inventors herein and co-workers, P. Pekala and M. D. Lane, 3T3-L1 preadipocytes, originally cloned from mouse embryo fibroblasts, differentiate in monolayer culture into cells having the biochemical and morphological characteristics of adipocytes. During adipocyte conversion, 3T3-L1 cells exhibit a coordinate rise in the enzyme of de novo fatty acid synthesis and triacylglycerol synthesis. Similarly, the activity of lipoprotein lipase, another key enzyme of lipid metabolism, rises 80–180 fold during adipose conversion. The activity of the enzyme is enhanced by the presence of insulin in the medium and appears to be similar to the lipoprotein lipase of adipose tissue.

Utilizing cells of the 3T3-L1 preadipocyte cell line, it was found that addition of the mediator compositions, derived from mouse peritoneal exudate cells exposed to endotoxin as described above, suppresses the activity of lipoprotein lipase.

The endotoxin used in the 3T3-L1 cell culture study was obtained as described above. Cell culture media and fetal calf serum were obtained from Gibco Laboratories (Long Island, N.Y.). 3-isobutyl-1-methylxanthine was from Aldrich Chemical (Milwaukee, Wis.), dexamethasone from Sigma Chemical Company (St. Louis, Mo.), and insulin from Eli Lilly Corporation (Arlington Heights, Ill.). Triolein was from Nu Check Prep, Inc. (Elysian, Minn.). Crystaline bovine serum albumin was from Calbiochem-Behring Corporation (LaJolla, Calif.).

I. 3T3-L1 Cell Culture:

3T3-L1 preadipocytes were cultured as previously described [MacKall, et al., J. BIOL. CHEM. 251 at 6462 (1976), and A. K. Student, et al., J. BIOL. CHEM., 255 at 4745–4750 (1980)] in Dulbecco's modified Eagle's medium (DME medium) containing 10% fetal calf serum. Differentiation leading to the adipocyte phenotype was induced by the Student, et al., modification of the method of Rubin, et al., [J. BIOL. CHEM. 253 at 7570–7578 (1978)]. Two days after confluence, the medium was supplemented with 0.5 mM isobutyl-methylxanthine, 1 $\mu$M dexamethasone and 10 $\mu$g of insulin per ml. Forty-eight hours later, the medium containing isobutyl-methylxanthine, dexamethasone, and insulin was withdrawn and replaced with medium containing insulin at a reduced concentration of 50 ng per ml.

J. Effect of Mediator Compositions on 3T3-L1 Cells:

One hour after the culture medium was replaced with medium containing the reduced concentration of insulin, conditioned media from cultured exudate cells with or without added endotoxin were added to 3T3-L1 cell cultures. Incubation of the cells with the conditioned medium was carried out for up to 20 hours. At indicated times, the amount of lipoprotein lipase activity was measured in three compartments: (1) the activity of the medium; (2) the activity released from the cells following incubation with heparin (this activity represents the enzyme associated with the outer surface of the cell membrane); and (3) intracellular activity.

Following the withdrawal of the medium, the dishes were rinsed once with fresh medium and the lipoprotein lipase associated with the cell membrane was released by incubation for one hour in DME medium supplemented with heparin (10 U/ml) and insulin (50 ng/ml). After removing this medium, the dishes were rinsed with PBS and the cells were scraped into 1 ml of 50 mM, $NH_3/NH_4Cl$ buffer, pH 8.1 containing heparin 3 U/ml. The cell suspension was sonicated (on ice) for 15 seconds and centrifuged at 500×g for 5 minutes. The supernatant was assayed for lipoprotein lipase.

Lipoprotein lipase assays were performed within 30 minutes after the preparation of each sample in duplicate by the method of Nilsson-Ehle and Shotz [J. LIPID. RES. 17 at 536–541 (1976)] with minor modifications. Briefly, 75 $\mu$l of enzyme was mixed with 25 $\mu$l of substrate containing 22.7 mM[3H]-triolein (1.4 uCi per mole), 2.5 mg per ml of lecithin, 40 mg per ml bovine serum albumin, 33% (V/V) human serum and 33% (V/V) glycerol in 0.27 M Tris-HCl, pH 8.1, and incubated at 37° C. for 90 minutes. One milliunit of enzyme activity was defined as the release of one nanomole of fatty acid per minute. The lipase activity in all three compartments was inhibited >90% by addition of 1 M NaCl and >80% by omission of serum which is the source of apolipoprotein C-II needed for enzymatic activity.

To test the effect of the mediator on the lipoprotein lipase activity of 3T3-L1 cells, the conditioned medium obtained from mouse peritoneal exudate cells cultured in the presence or absence of endotoxin, was added to 3T3-L1 cells in monolayer culture. After a 20-hour incubation at 37° C., lipoprotein lipase activity was assessed in three compartments: (1) the culture medium; (2) the cell surface (heparin-releasable lipase activity) and; (3) the intracellular fraction.

Figure 3:
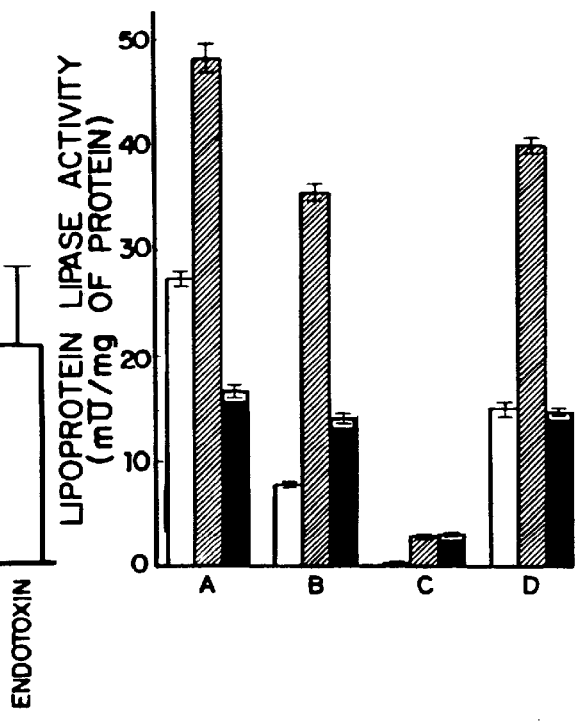
FIG. 3 shows the effect of conditioned medium from endotoxin-treated mouse peritoneal exudate cells over lipoprotein lipase activity of 3T3-L1 cells. Data are expressed as mean SEM (n=4).
Figure 6A:
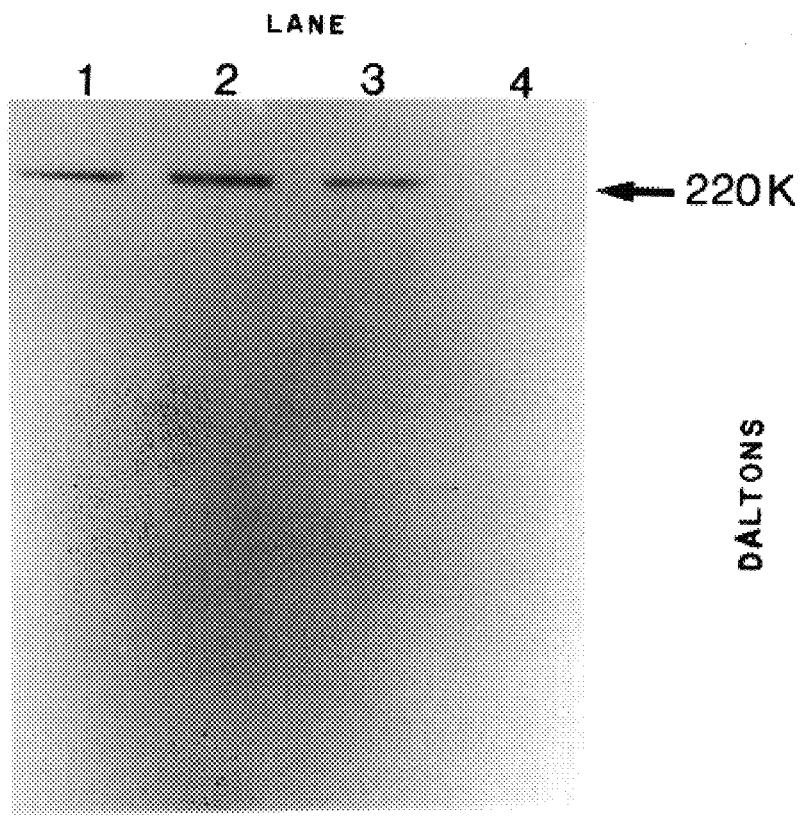
FIGS. 6A and 6B show the effect of a mediator that suppresses the synthesis of fatty acid synthetase. Experimental design is identical to that described in the legend to FIG. 5. Panel A: Autoradiogram of a 7.5%-acrylamide-SDS gel analysis of immunoadsorbable fatty acid synthetase. Lane 1—control, without exposure to mediator; Lanes 2, 3, and 4, exposure of the cells to the mediator for 3, 6 and 20 hours, respectively. Panel B: Results of a densitometric scan of the autoradiogram, indicating percent of immunoadsorbable material remaining relative to control after exposure to the mediator.
Figure 6B:
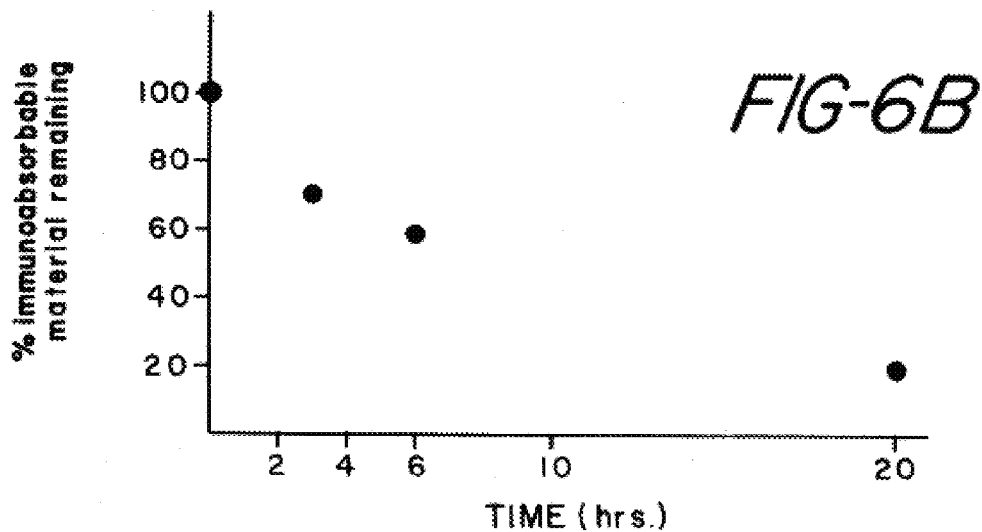
Figure 7:
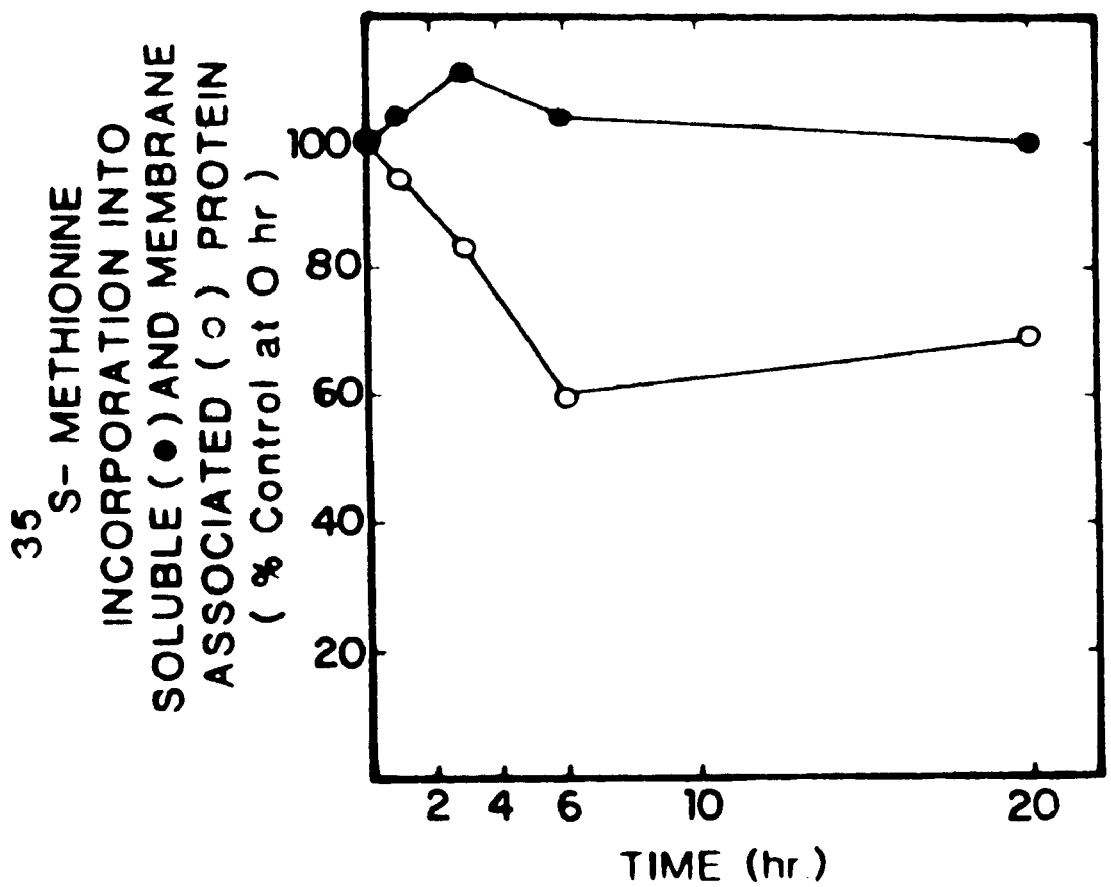
FIG. 7 shows the effect of the mediator on $^{35}$S-methionine incorporation into protein. 3T3-L1 cells were incubated with 300 µl of conditioned medium from endotoxin-treated mouse peritoneal exudate cells for the appropriate period and protein pulse-labeled with 0.5 mCi of $^{35}$S-methionine for 1 hour. Soluble proteins were obtained by digitonin treatment of the cells, the remainder of the monolayer was extracted with NP-40 and a membrane protein fraction obtained. Incorporation of $^{35}$S-methionine into acid precipitable material was determined as described in Example II, infra. The incorporation of radioactivity into soluble protein (•) or membrane protein (○) following exposure of the cells to the mediator are shown for the indicated time.
Figure 8:
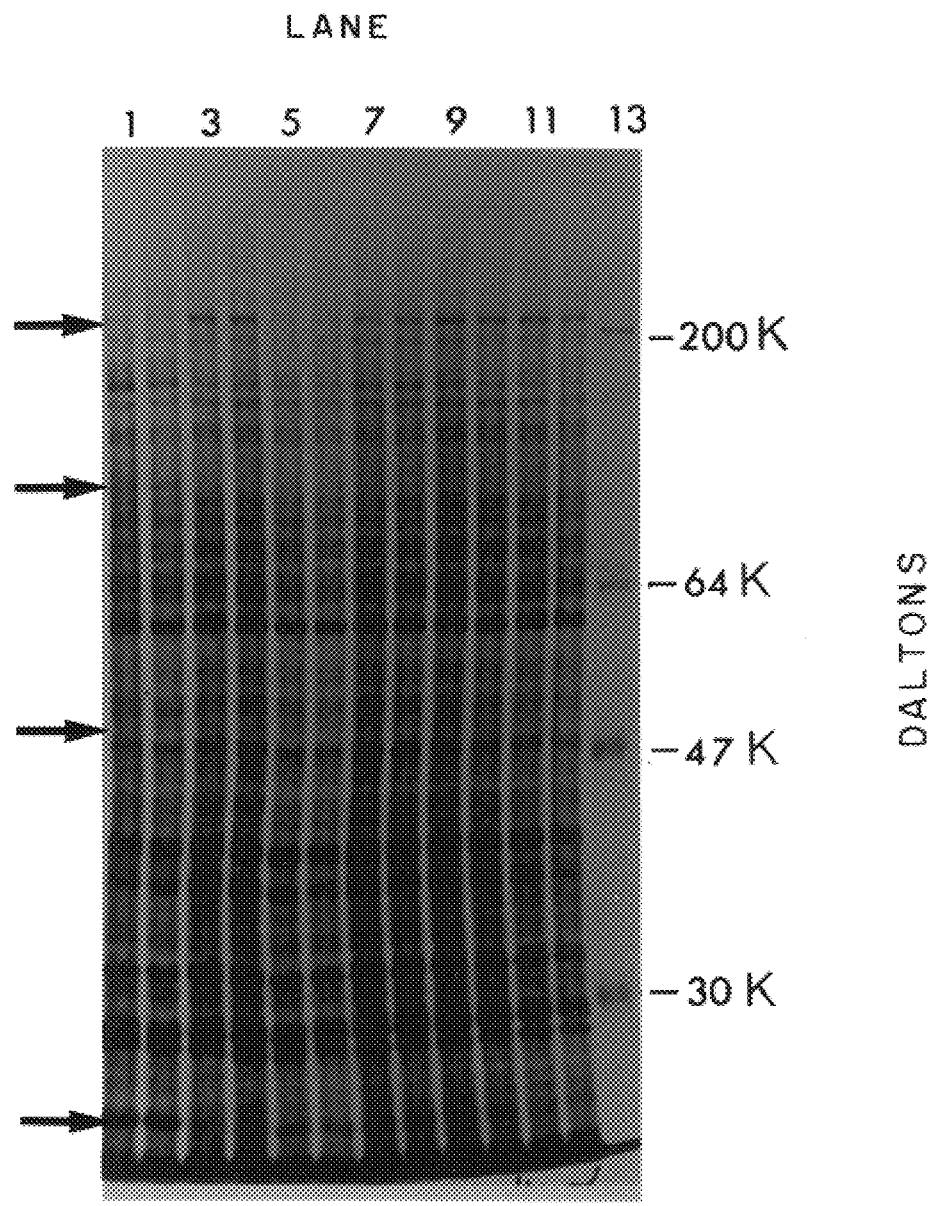
FIG. 8 shows the effect of mediator on protein synthesis in the cytosolic fraction of the cells. Autoradiogram of a 7.5%-acrylamide-0.1% SDS gel analysis of 35S-methionine labeled cytosolic protein after exposure of the cells to the mediator. 3T3-L1 cells were pulse labeled and the soluble protein was obtained by digitonin as described in Example II. Aliquots ($2 \times 10^5$ cpm) of the cytosolic fraction for each time point were applied to the gel and electrophoresed. Lanes 1 and 2, control without exposure to mediator; Lanes 3 and 4, 1 hour exposure to the mediator; Lanes 5 and 6, 3 hours of exposure; Lanes 7 and 8, 6 hours of exposure; Lanes 9 and 10, 20 hours of exposure to conditioned medium from mouse peritoneal exudate cells not exposed to endotoxin; Lanes 11 and 12, exposure of cells to mediator for 20 hours
Figure 9:
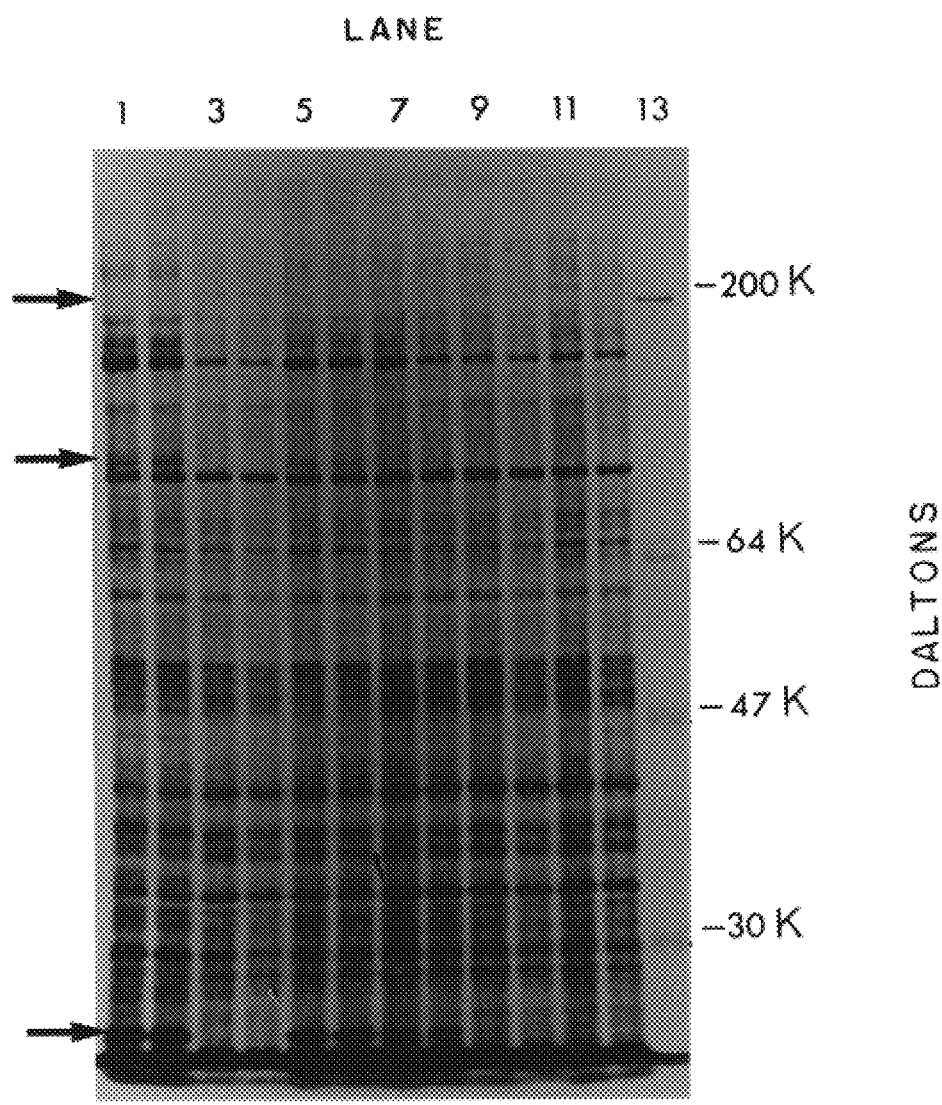
FIG. 9 shows the effect of mediator on protein synthesis in the membrane fraction of the cells. Autoradiogram of a 7.5%-acrylamide-0.1% SDS gel analysis of $^{35}$S-methionine labeled membrane protein after exposure of the cells to the mediator. Experimental design was identical to that described in the legend to FIG. 8. Membrane proteins were obtained by NP-40 extraction as described in Example II. Lanes 1 and 2—control, without exposure to mediator; Lanes 3 and 4, 1 hour of exposure to the mediator; Lanes 5 and 6, 3 hours of exposure; Lanes 7 and 8, 6 hours of exposure; Lanes 9 and 10, 20 hours of exposure of the cells to conditioned medium from mouse peritoneal exudate cells not exposed to endotoxin; Lanes 11 and 12, exposure to mediator for 20 hours.

As shown in FIG. 3, Cols. A & C, the addition of media containing the mediator substance from endotoxin-stimulated exudate cells, markedly suppressed the lipoprotein lipase activity in all three compartments. The enzyme activities in the medium, on the cell surface (heparin releasable), and in the intracellular compartment were 0.1%, 6%, and 18%, respectively, of that of the control cells incubated with the same amount of fresh RPMI-1640 medium. No difference in morphology or extent of adipocyte conversion was detected between cells in the experimental and control groups. At the beginning of the study, approximately 20% of the cells exhibited triglyceride accumulation in the cytoplasm; 20 hours later, approximately 50% of both the experimental and control cells had accumulated triglyceride.

The medium from the culture of exudate cells not treated with endotoxin had little effect on the lipoprotein lipase activity of 3T3-L1 cells. While the medium from untreated exudate cells elicited some inhibition in the study shown in FIG. 3, Col.B in other similar studies, medium prepared identically had no inhibitory effect. Endotoxin itself also had a negligible inhibitory effect on lipoprotein lipase activity when the amount added was equivalent to that which might remain in the conditioned medium from endotoxin-treated exudate cells; a 19%, 9%, and 0% decrease was observed on medium, heparin-releasable and intracellular compartments, respectively. The decrease was greater (45% in medium, 17% in heparin-releasable, and 11% in the cells) when larger amounts (4.5 times) of endotoxin was employed, as shown in FIG. 3, Column D.

A possible explanation for the decreased activity of lipoprotein lipase described above is a direct inhibitory effect of mediators on the enzyme. This was examined by incubating medium from 3T3-L1 cell cultures which contained lipoprotein lipase with conditioned medium from cultures of endotoxin-treated exudate cells. It was found that the enzyme activity was not inhibited by the mediator compositions (103% of the control) at the time of mixing, and the rate of decay of enzyme activity was the same in the experimental group and the control group. Endotoxin also had no effect on the activity of lipoprotein lipase. The results imply that the mediator compositions depress lipoprotein lipase activity in 3T3-L1 cells by inhibiting the intracellular synthesis or processing of the enzyme.

The relationship between the amount of mediator compositions and lipoprotein lipase activity of 3T3-L1 cells was examined by incubating the cells with increasing amounts of the conditioned medium from endotoxin-treated exudate cells for 20 hours at 37° C. Ten $\mu$l of conditioned media added to 1.5 ml of culture media was sufficient to cause a substantial decrease in lipoprotein lipase activity, i.e., 57% decrease in the medium, 40% decrease in the heparin-releasable compartment, and 8% decrease in the cells. Enzyme activity was further depressed by increasing the amount of mediator containing medium. When 250 $\mu$l were added, a decrease of greater than 95% was observed in all three compartments. The amount of mediator present in conditioned medium varied somewhat from preparation to preparation.

The rate at which lipoprotein lipase activity declines after the addition of the mediators was also investigated. Conditioned medium containing mediators was added at selected intervals, and lipoprotein lipase activity was measured. A reduction of lipase activity was apparent as early as 30 minutes after addition of 3T3-L1 cells. Approximately half of the intracellular enzyme activity was lost after 2.5 hours. After 5 hours of incubation with a mediator, a maximal effect was observed. The amount of enzyme activity in the medium and that on the cell surface were also observed to decrease with a similar time course (data not shown).

The rapid decrease in lipoprotein lipase activity might reflect a competition with insulin since removal of insulin has been shown to lead to a rapid decline in lipoprotein lipase activity in 3T3-L1 cells. However, an attempt was made to reverse the suppressive effect of the mediator by increasing the concentration of insulin in the medium was not successful. For this study, the effect of incubating 3T3-L1 cells with media containing insulin at various concentrations (50 ng/ml to 50 $\mu$g/ml) and mediator was assessed for lipoprotein lipase activity. It was found that the inhibitory effect of the mediator on enzyme activity was not changed with increasing insulin concentrations. Even at an insulin concentration 1,000 greater (50 $\mu$g/ml) than that of standard onditions (50 ng/ml), the inhibition was not reversed.

EXAMPLE II

Reasoning that other anabolic activities of the 3T3-L1 cells might be inhibited by the mediator, we studied two key enzymes: (1) acetyl CoA carboxylase; and (2) fatty acid synthetase; for de novo fatty acid biosynthesis. The following example based upon a manuscript in preparation by the inventors herein and co-workers, P. Pekala, M. D. Lane and C. W. Angus, presents evidence that the synthesis of these enzymes are also inhibited by the addition of the macrophage mediator. The results implicate a larger role for the mediator(s) and point to the presence of a communication system between immune cells and energy storage cells of mammals. Presumably, during invasion the immune cells can function as an endocrine system and selectively mobilize energy supplies to combat the invasion.

A. Materials:

Endotoxin (lipopolysaccharide) from *E. coli* 0127: B8 isolated by the method of Westphal, described supra, was purchased from Difco Laboratories (Detroit, Mich.). Cell culture media and fetal calf serum were obtained from Gibco Laboratories (Grand Island, N.Y.). 3-isobutyl-1-methylxanthine was from Aldrich Chemical (Milwaukee, Wis.); dexamethasone, from Sigma Chemical Company (St. Louis, Mo.); and insulin from Eli Lilly (Indianapolis, Ind.). IGG-SORB was from the Enzyme Center, Inc., (Boston, Mass.). L-[$^{35}$S]Methionine (800–1440 Ci/mmol) was from Amersham, En $^3$Hance was obtained from NEN, (Boston, Mass.). Antiserum to fatty acid synthetase was kindly provided by Dr. Fasal Ashmad of the Papanicolau Cancer Research Institute, Miami, Fla.

B. 3T3-L1 Cell Culture:

3T3-L1 preadipocytes were cultured as previously described, [MacKall, et al., J. BIOL. CHEM. 251 at 6462 (1976)] in Dulbecco's modified Eagle's medium (DME medium) containing 10% fetal calf serum. Differentiation leading to the adipocyte phenotype was induced by the Student, et al., modification (A. K. Student, et al., J. BIO. CHEM. 255 at 4745–4750 (1980)) of the method of Rubin, et al., J. BIOL. CHEM. 253 at 7570 (1978). Two days after confluence, the medium was supplemented with 0.5 mM isobutyl-methylxanthine, 1 $\mu$M dexamethasone and 10 $\mu$g of insulin per ml. Forty-eight hours later, the medium containing isobutyl-methylxanthine, dexamethasone, and insulin was withdrawn and replaced with medium containing insulin at a reduced concentration of 50 ng per ml.

C. Preparation of Peritoneal Exudative Cells and Mediator Substances:

Peritoneal exudate cells were obtained by peritoneal lavage from C3H/HeN mice (25–33 g; Charles River Breeding Laboratories, Wilmington, Mass.) which had been injected intraperitoneally with sterile Brewer's thioglycollate medium (Difco Laboratories, Detroit, Mich.; 3 ml per mouse) 6 days prior to harvest. The exudate cells obtained using this procedure are primarily macrophages with some contaminating lymphocytes, The cells ($4 \times 10^5$ cells per $cm^{2d}$) were incubated in serum-free RPMI-1640 medium for 3 hours after which nonadherent cells were removed by washing 3 times with medium. Cells adhering to the dish were primarily macrophages. These cells were further incubated in serum-free RPMI-1640 medium in the presence or absence of 10 µg per ml of endotoxin. After 24 hours, the culture medium was removed and centrifuged at 1,000×g for 5 minutes at 4° C. The supernatant of conditioned medium obtained from cells exposed to endotoxin was assayed and found to contain the mediator substance that lowers LPL in 3T3-L1 cells.

No difference in activity was noted after storage of the conditioned medium for one month at −80° C.

D. Effect of Mediator on 3T3-L1 Cells:

One hour after the culture medium was replaced with medium containing the reduced concentration of insulin, conditioned media from cultured exudate cells with or without added endotoxin were added to 3T3-L1 cell cultures. Incubation of the cells with the conditioned medium was carried out for up to 20 hours.

E. Labeling of Cellular Proteins:

A 6-cm plate containing induced 3T3-L1 cells was washed twice with 5 ml of methionine-free medium and incubated for 1 hour with 2 ml of the same medium containing 0.5 mCi of L-[$^{35}$S]-methionine during which period the rate of [$^{35}$S]-methionine incorporation into cellular protein was linear. The medium was removed, the cell monolayer washed twice with phosphate-buffered saline, ph 7.4, and the soluble cytosolic proteins released by the digitonin method of Mackall, et al, supra. The remainder of the cell monolayer containing the membranous fraction was then scraped into 2.0 ml of 100 mM HEPES buffer, pH 7.5, containing 0.5% of the nonionic detergent NP-40 and 1 mM phenylmethylsulfonylfluoride. After trituration in a Pasteur pipet, the suspension was centrifuged at 10,000×g for 10 minutes at 4° C., and the supernatant saved.

[$^{35}$S]-methionine incorporation into acid insoluble material was determined by adding 20 µl of digitonin or NP-40 released material to 0.5 ml of ice cold 20% TCA with 25 µl of 0.5% bovine serum albumin added as carrier. After sitting at 4° C. for 1 hour, the mixture was centrifuged at 2,000×g for 5 minutes. The pellet was incubated in 0.5 ml of 1 M NH$_4$OH at 37° C. for 30 minutes. The protein was reprecipitated on addition of 5.0 ml of ice cold 10% TCA and filtered on Whatman GF/C filters. The filters were extracted with diethyl ether and the amount of radiolabel determined.

F. Immunoadsorption Electrophoresis:

Aliquots of the soluble [$^{35}$S]-methionine-labeled proteins from the soluble (digitonin released) fraction of the cell monolayer were made 1 mM in PMSF and 0.5% in NP-40 detergent and then added to 5-1 of either antisera specific for acetyl CoA carboxylase, or fatty acid synthetase, After 2 hours at 25° C., 100 µl of 10% IgG-SORB were added and the labeled enzymes isolated from the mixture by the method of Student, et al., supra. Polyacrylamide-SDS gels were run according to the method of Laemmli, and prepared for fluorography by use of En$^3$Hance according to the manufacturer's instructions.

G. Results—Effect of Mediator on Acetyl CoA Carboxylase and Fatty Acid Synthetase:

To examine the effect of the mediator substance on the activities of acetyl CoA carboxylase and fatty acid synthetase enzymes, 3T3-L1 cells were exposed to conditioned medium from mouse peritoneal exudate cells cultured in the presence of endotoxin. After incubation of the 3T3-L1 cells with the mediator for 3, 6 and 20 hours, acetyl CoA carboxylase and fatty acid synthetase activities were determined on a digitonin released cytosolic fraction of the cells (FIG. No. 4). The activity of both enzymes decreased over the 20-hour period to approximately 25% of the initial values.

To determine if the loss in activity of the two enzymes was a result of a direct effect on protein synthesis, 3T3-L1 cells were incubated with conditioned medium from cultures of endotoxin-treated exudate cells for 3, 6, and 20 hours. During the final hour of incubation, the cells were exposed to a pulse of $^{35}$S-methionine. Following the pulse, $^{35}$S-methionine labelled acetyl CoA carboxylase and fatty acid synthetase were isolated from the digitonin releasable cytosolic fractions by immunoadsorption. Identification was accomplished by SDS-polyacrylamide gel electrophoresis and fluorography (FIGS. No. 5A and 6A). The decreased incorporation of $^{35}$S-methionine into immunoadsorbable acetyl CoA carboxylase and fatty acid synthetase with respect to time following exposure to the mediator is readily observed. Densitometric scanning of the autoradiograms (FIGS. No. 5B and 6B) indicated that after 20 hours of exposure to the mediator, the amount of $^{35}$S-methionine incorporated into fatty acid synthetase and acetyl CoA carboxylase were decreased by 80% and 95% respectively. These results are consistent with the concept that the mediator depresses the activity of acetyl CoA carboxylase and fatty acid synthetase by interfering with the synthesis of the enzyme.

H. Effect of Mediator on Protein Synthesis in General:

The observed effect on acetyl CoA carboxylase and fatty acid synthetase could be explained by a general inhibition of protein synthesis by the mediator. To examine this possibility, the effect of mediator on amino acid incorporation into protein was investigated. 3T3-L1 cells were incubated for various periods of time with conditioned medium obtained from mouse peritoneal exudate cells cultured in the presence of endotoxin. $^{35}$S-methionine incorporation into soluble and membrane associated protein was determined after 1, 3, and 6 hours of exposure of the cells to the added factor. When 3T3-L1 cells were exposed to conditioned medium from mouse peritoneal exudate cells that were cultured in the absence of endotoxin, no effect on $^{35}$S-methionine in incorporation into acid insoluble protein was observed. However, as seen in FIG. No. 7, $^{35}$S-methionine incorporation into TCA precipitable material in the soluble fraction (Digitonin releasable protein) increased approximately 10% in the first 3 hours with no further change observed, while a 50% decrease was observed for label incorporation into acid insoluble material in the membrane fraction (NP-40 solubilized protein). Analysis of $^{35}$S-methionine labeled proteins following exposure to the mediator was accomplished utilizing SDS-gel electrophoresis. The pattern of the autoradiogram of the soluble proteins obtained on digitonin treatment and those solublized by NP-40 of the 3T3-L1 cells are shown in FIGS. No. 8 and 9. Closer inspection of FIG. No. 8 reveals the gradual disappearance with time following the addition of the mediator of a protein band with a molecular weight of 220,000 Daltons, while another band appears at approximately 18,000. In addition to these major changes, another new protein appears at approximately 80,000 while a second protein of 50,000 disappears.

Analysis of the NP-40 solubilized proteins showed similar results (FIG. No. 9). Protein bands of molecular weights of approximately 80,000 and 30,000 Daltons appeared while bands of approximately 220- and 50,000 disappeared.

The loss of a protein band with molecular weight 220,000 in the digitonin releasable protein, is consistent with the loss of immunoadsorbable acetyl CoA carboxylase and fatty acid synthetase. The enzymes have similar molecular weights and under the conditions of this electrophoresis migrate with the same Rm. At present, it is not possible to identify the other protein bands with known enzymes or proteins.

I. Analysis.

The mediator appears to decrease enzymatic activity by suppressing the synthesis of the enzymes. The effect on protein synthesis appears to be quite specific as there are no gross perturbations of the protein patterns observed on the autoradiograms (FIGS. No. 8 and 9). In response to the mediator, the synthesis of several proteins is inhibited or induced. It was possible by immunoprecipitation to identify fatty acid synthetase and acetyl CoA carboxylase (M.W. 220,000) as two proteins whose synthesis is inhibited by the mediator. The identification of the other proteins that are modulated by the mediator is not possible at present, although lipoprotein lipase is a potential candidate for the 50,000-Dalton protein that appears. The nature of proteins that are induced in response to the mediator and the mechanism for the modulation of specific protein synthesis are deserving of further improvement investigations.

Whether the mediator responsible for regulating the synthesis of acetyl CoA carboxylase and fatty acid synthetase is the same as the mediator that suppresses the activity of lipoprotein lipase is not presently known. The relationship of these mediator(s) to the leukocyte factor that has been reported to metabolize amino acids from muscle to the liver is of considerable interest since this factor also imparts a catabolic state on the tissue.

EXAMPLE III

In this series of investigations, also embodied in an unpublished manuscript in preparation by the inventors herein, and co-worker Shigeru Sassa, we sought to determine whether the macrophage mediator(s) observed in Examples I and II exerted any effect upon red blood cell synthesis. We reasoned that, as anemia is commonly observed in mammals afflicted with chronic infections, and that as regeneration of the red cell mass constitutes a potential drain on energy and amino acids, the body in response to acute invasion may interrupt erythroid development in similar fashion and perhaps by the same mechanism observed with respect to the anabolic enzymes lipoprotein lipase, acetyl Coenzyme A carboxylase and fatty acid synthetase, that affect adipocytes.

To evaluate this hypothesis, we examined the effects of endotoxin-induced factor(s) from mouse macrophages on the cellular proliferation and differentiation of a model erythroid progenative cell—the Friend virus- transformed erythroleukemia cells (See Friend, C. et al and Marks, P. A. et al., supra.). In this model system, cells can be induced to differentiate and form hemoglobin in response to a number of inducers, such as dimethylsulfoxide, (Friend, C., et al supra.), hexamethylenebisacetamide (Reuben, R. C. et al, PROC. NATL. ACAD. SCI., U.S.A., 73: 862–866),butyric acid, (Leder, A. et al (1975) Cell 5:319–322), and hypoxanthine (Gusella, J. F. (1976) Cell 8:263–269). This example presents evidence that a macrophage mediator(s) can inhibit the growth and differentiation of erythroid committed cells, but has less effect on uncomitted stem cells and practically no effect on fully differentiated erythroid cells.

A. Materials:

Endotoxin (lipopolysaccharide) from $E\ coli$ 0127: B8 isolated by the method of Westpal (described supra.), was purchased from Difco (Detroit, Mich.). A modified F12 medium was prepared in our laboratory (Sassa, S. et al, J. BIOL. CHEM. 252: 2428–2436 (1977)). Fetal bovine serum was purchased from GIBCO (Grand Island, N.Y.). Dimethylsulfoxide($Me_2SO$) was a product of Eastman Organic Chemicals (Rochester, N.Y.). Butyric acid and hypoxanthine were obtained from Sigma Chemical Company (St. Louis, Mo.). Hexamethylenebisacetamide (HMBA) was kindly provided by Dr. R. C. Reuben, Merck Sharp & Dohme Research Laboratories (Rahway, N.J.).

B. Cell Culture:

Murine Friend-virus transformed erythroleukemia cells (clone DS-19) were cultivated in modified F12 medium supplemented with 10% heat inactivated fetal bovine serum as described previously (Sassa, S.,Granick, J. L.,Eisen, H. and Ostertag,W. (1978). In In vitro Aspects of Erythropoiesis, ed. by Murphy, M. J. Jr. (Springer-Verlag, New York) pp. 268–270).

C. Preparation of the Endotoxin-Stimulated Conditioned Medium From the Culture of Mouse Exudative Cells:

Isolation of peritoneal exudate cells from NCS mice (25–33 g from the Rockefeller University Breeding Colony) and preparation in vitro of an endotoxin-stimulated conditioned medium were carried out as described (in Example I, above). Briefly, peritoneal exudate cells were isolated from mice treated with sterile Brewer's thioglycollate medium obtained from Difco Laboratories (Detroit, Mich.),in an amount of 3 ml per mouse, 6 days prior to harvest. The cells were incubated in serum-free RPM1–1640 medium for 3 hours, after which non-adherent cells were rinsed off by washing three times with medium. Cells adhering to the dish were primarily macrophages (Kawakami et al., PROC. NATL. ACAD. SCI., USA 79:912–916; Edelson, P. S. et al., J. EXP. MED., 142:1150–1164 (1975)).

These cells were further incubated in the serum-free medium in the presence of endotoxin (5 $\mu$g/ml) for 24 hours. After incubation, the culture medium was removed and centrifuged at 1000×g for 5 minutes at 4° C. The supernatant of the conditioned medium contained an endotoxin-induced mediator which decreased the activity of lipoprotein lipase in 3T3-L1 cells (as reported in Example I, above) and was used without further treatment.

D. Induction of Erythroid Differentiation:

Two types of incubation protocols were used to assess erythroid differentiation of Friend cells. In certain experiments illustrated in FIGS. 10–13, the cells ($5\times10^4$ cells/ml) were incubated at 37° C., in 5% $CO_2$ in humidified air for 18 hours. The inducing chemicals, e.g. $Me_2SO$, HMBA, butyric acid, hypoxanthine or hemin were added with or without macrophage mediator(s) and cultures were incubated for 96 hours without changing the growth medium. In other experiments such as those with results illustrated in FIG. 14, the cells ($10^5$ cells/ml) were incubated for 18 hours, then $Me_2SO$ and the macrophage mediator were added as above. The cultures were maintained at $2\times10^5$ cells/ml by diluting the cell suspension daily with fresh medium containing the chemical inducer with or without the macrophage mediator. This procedure required more macrophage mediator than the first experimental procedure, but made it possible to examine the effect of mediator on rate of cell growth while cells were growing logarithmically at a constant rate (Chang, C. S. et al; J. BIOL. CHEM. 257:3650–3654 (1982)).

E. Determination of Heme Content and Assays on the Activities of Enzymes in the Hene Biosynthetic Pathway:

The concentration of heme in cells was determined by a fluorometric assay of porphyrin derivatives after the removal of iron (Sassa, S., Granick, S., Chang, C. and Kappas, A., In Erythropoisis, ed. by K. Nakao, J. W. Fisher and F. Takaku (University of Tokyo Press, Tokyo, Japan (1975) pp. 383–396). Cells containing hemoglobin were stained with benzidine and counted using a Cytograf model 6300A (Sassa, S. Granick, J. L., Eisen, H., and Ostertag, W., Supra.). Assays of aminolevulinic acid (ALA) dehydratase and porphobilinogen (PBG) deaminase were carried out by methods described previously (Sassa, S., Granick, J. H., Eisen, H., and Ostertag, W., Supra.).

Figure 10:
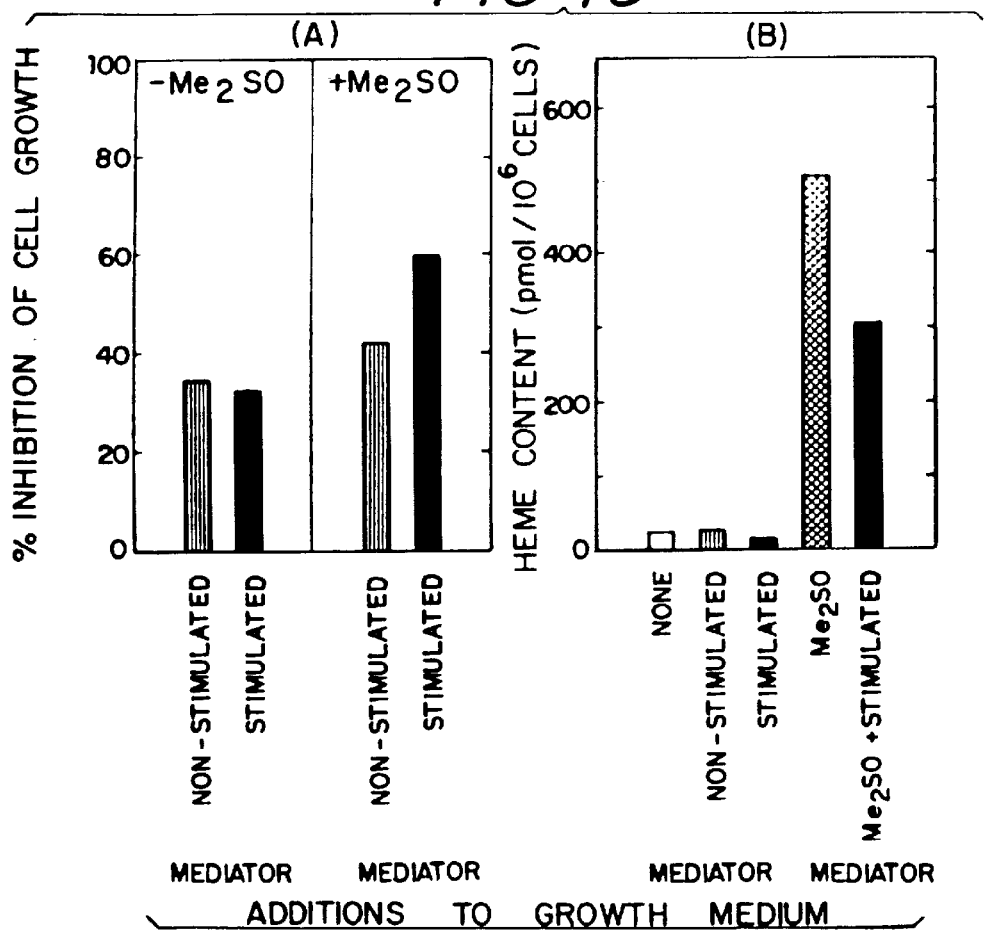
FIGS. 10A and 10B show the effect of conditioned media from mouse macrophage cultures on the cell growth and heme content in Friend cells.

F. Effects of the Macrophage Mediator on the Growth and Differentiation of Uninduced Friend Cells:

Conditioned media from macrophage cultures incubated with or without endotoxin inhibited the growth of untreated Friend cells by approximately 35% (FIG. 10, Part A.). When these cells were incubated simultaneously with 1.5% $Me_2SO$, control conditioned medium which had not been exposed to endotoxin inhibited the cell growth by ~42% while endotoxin-stimulated conditioned medium inhibited the growth of ~60% (FIG. 10, Part B).

Heme content in these cells treated with endotoxin-stimulated or non-stimulated conditioned media was not appreciably different from that found in untreated cells, indicating that the conditioned medium by itself does not affect the erythroid differentiation of Friend cells (FIG. 10, Part B), In contrast, incubation of cells with $Me_2SO$ and endotoxin-stimulated conditioned medium led to a significant decrease (~40%) in the heme content in the cell (FIG. 10, Part B).

Figure 11:
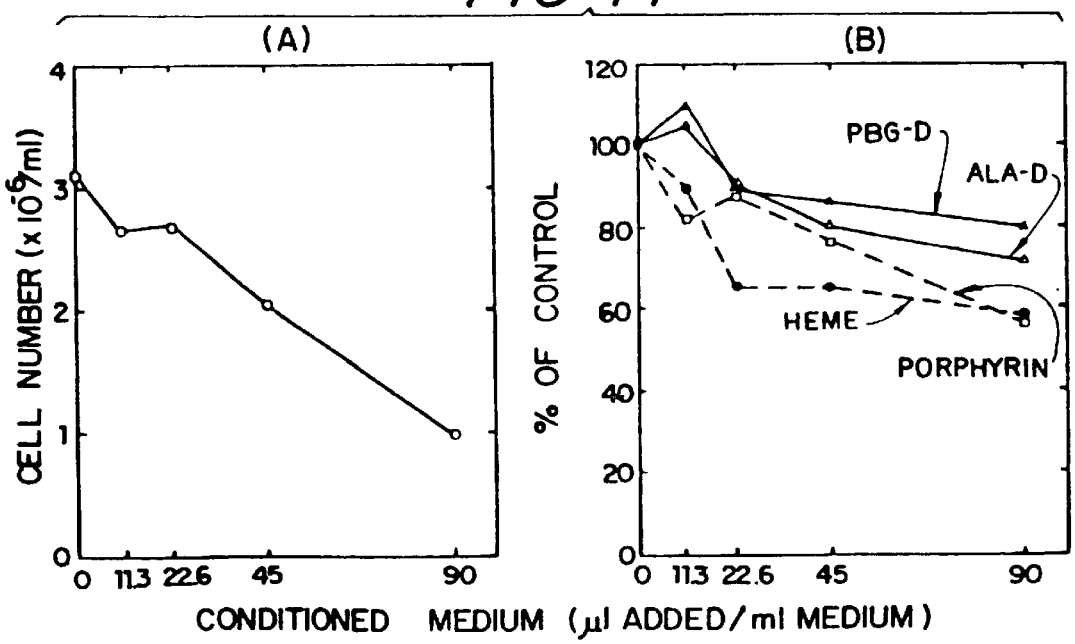

G. Dose Dependent Inhibition of Cell Growth and Differentiation By the Macrophage Mediator:

When Friend cells were incubated simultaneously with 1.5% $Me_2SO$ and the endotoxin-stimulated macrophage mediator, the rate of cell growth was progressively inhibited when increasing amounts of the mediator were added to the culture (FIG. 11, Part A). An inhibitory effect of the mediator on cell growth could be detected at the lowest concentration examined (1.12 vol. % added to growth medium), At the highest concentratio (8 vol. %), the mediator inhibited cell growth by ~60% compared with that of the control $Me_2SO$-treated culture (FIG. 11, Part A). The decrease in cell number was not due to cell death since the number of dead cells as assessed by the Trypan Blue exclusion test (Paul J. In Cell Culture) was similar (~8%) for untreated controls and cultures treated with the stimulated conditioned medium. Endotoxin itself (up to 15 $\mu$g/ml) exhibited no inhibitory effect on the growth of Friend cells either in the presence or in the absence of $Me_2SO$ (data. not shown). These findings indicate that the endotoxin-stimulated macrophage mediator interferes with the growth of $Me_2SO$-treated cells more than that of untreated cells and suggest that erythroid committed cells may be more sensitive than uncommitted stem cells to the action of the stimulated macrophage mediator.

Treatment of cells with the endotoxin-stimulated macrophage mediator inhibited $Me_2SO$-mediated erythroid differentiation resulting in a progressive decrease in the content of porphyrin and heme in the treated cells as the amount of the mediator increased, (FIG. 11, Part B.) The enzymatic activities of ALA dehydratase and PBG deaminase were also decreased by the mediator treatment (FIG. 11, Part B). The addition of the macrophage mediator directly to the enzyme assay mixture did not inhibit the activity of ALA dehydratase or PBG Deaminase(data not shown), ruling out a direct inhibitory effect on the activities of the enzymes.

H. Delayed Addition of the Endotoxin-Stimulated Macrophage Mediator on Erythroid Differentiation:

When the endotoxin-stimulated conditioned medium was added to $Me_2SO$-treated cultures at various times, it was found that the effect of the macrophage mediator on cell growth was gradually lost (FIG. 12).

The effect of the macrophage mediator on erythroid differentiation decreased more rapidly than the effect on cell growth. For example, the addition of the endotoxin-stimulated macrophage mediator inhibited heme and protoporphyrin formation by ~40% at the beginning of incubation, ~25% when added at 24 hours, and had no effect when added at 48 hours or after. Inhibition of the activity of ALA dehydratase and PBG deaminase by the macrophage mediator treatment was also progressively diminished when the mediator was added later during incubation (FIG. 12).

These findings indicate that, in contrast to the macrophage-mediator dependent inhibition of cell growth and differentiation observed in erythroid-committed cells, cells which have fully expressed erythroid characteristics such as those exhibiting maximal increases in the activities of ALA dehydratase and PBG deaminase, or in the contents of protoporphyrin and heme, are considerably less sensitive to the inhibitory effect of the macrophage mediator.

Figure 13:
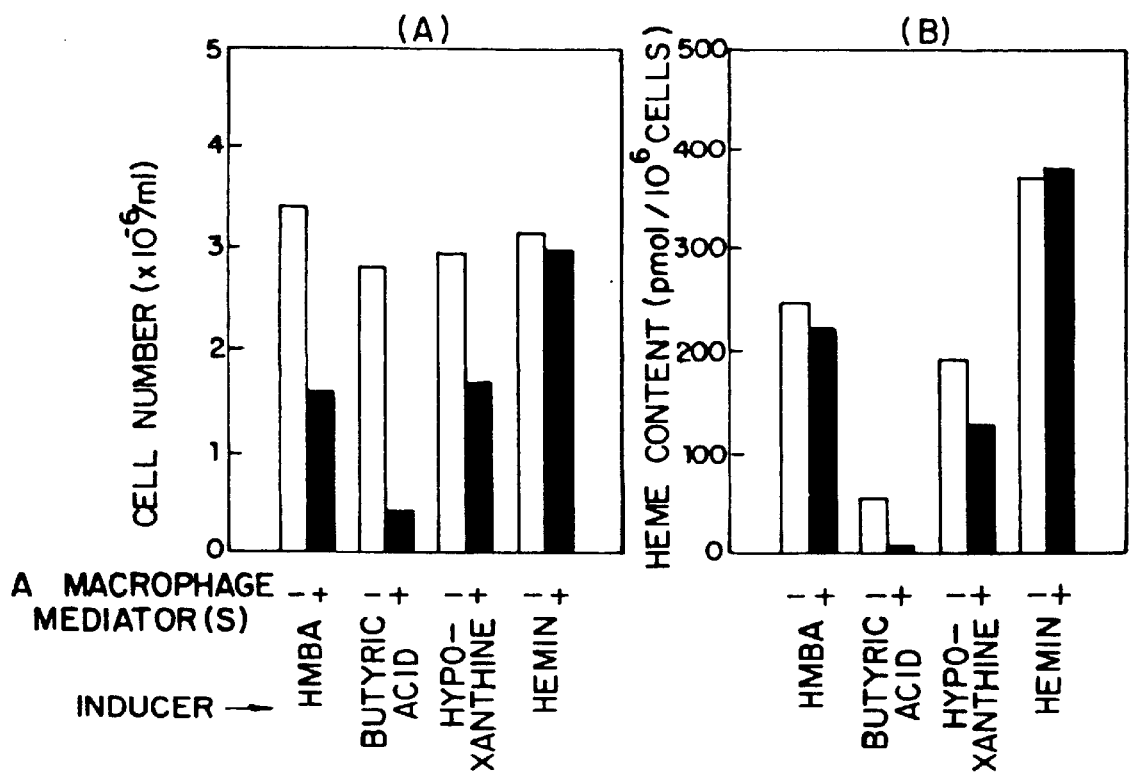

I. Effects of the Endotoxin-Stimulated Macrophage Mediator on Erythroid Differentiation of Friend Cells Induced by HMBA, Butyric Acid, Hypoxanthine or Hemin:

In order to examine whether or not the inhibitory effect of the endotoxin-stimulated macrophage mediator on erythroid committed cells is specific for $Me_2SO$-induced differentiation, we examined the effect of the macrophage mediator on cells which were incubated with either HMBA, butyric acid, hypoxanthine or hemin. We found that the endotoxin-stimulated macrophage mediator markedly inhibited the growth of cells incubated with HMBA, butyric acid or hypoxanthine, but not the growth of hemin-treated cells (FIG. 13, Part A). Similarly, the endotoxin-stimulated mediator inhibited the erythroid differentiation induced by HMBA, butyric acid or hypoxanthine, but not that induced by hemin treatment (FIG. 13, Part B).

These findings suggest that the inhibitory action of the endotoxin-stimulated macrophage mediator on the growth of erythroid-committed cells and erythroid differentiation induced by most of the chemical agents as represented by $Me_2SO$, HMBA, butyric acid or hypoxanthine is similar, but that erythroid differentiation induced by hemin treatment is distinct in nature and not sensitive to the effect of the macrophage mediator. In fact the growth inhibition of $Me_2SO$-treated cells produced by the macrophage mediator alone (35%, FIG. 10) was completely overcome by hemin treatment (FIG. 13).

J. Effect of Endotoxin-Stimulated Macrophage Mediator on the Growth and Differentiation of Friend Cells Growing at a Constant Rate:

In order to examine the effect of the macrophage mediator on the growth of Friend cells while they are growing at a constant rate, cells were diluted with fresh medium with or without the mediator every 24 hours to reduce the cell density to $2 \times 10^5$ cells/ml.

Figure 14:
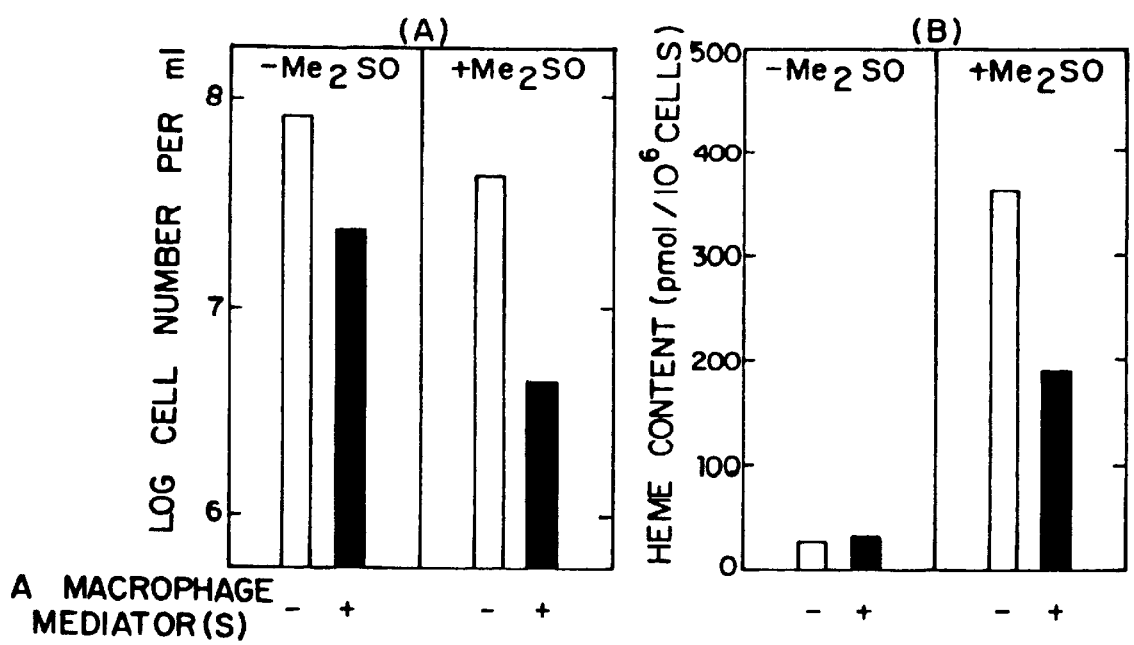

Under these conditions of culture, the cells maintain a continuous logarithmic growth at a constant rate (Chang, C. S. et al supra.). The total number of cells that would have formed from the original untreated control culture was $82 \times 10^6$ cells/ml after 96 hours of incubation (FIG. 14). The addition of the macrophage mediator significantly inhibited (~70%) cell growth. The addition of $Me_2SO$ to the cultures yielded $42 \times 10^6$ cells/ml. This decrease probably reflects the growth cessation which is associated with terminal erythroid differentiation of these cells. (Chang, C. S. supra.; Lo, S. C., Aft, R. and Mueller, G. C., Cancer Res. 41: 864–870 (1981)). Combined addition of $Me_2SO$ and the macrophage mediator produced the most profound growth inhibition (~90%) of these cells. Heme content in cells treated with the mediator alone was not appreciably affected while the combined treatment with the mediator and $Me_2SO$ brought about ~40% inhibition of heme formation.

K. Analysis:

The mediator substance under study appears to potently inhibit the growth and erythroid differentiation of mouse Friend-virus transformed cells. Conditioned medium from cultures not exposed to endotoxin had some inhibitory effects, but the effect of the endotoxin-stimulated conditioned medium is significantly greater in inhibiting the growth and differentiation of Friend cells. Endotoxin itself had no effect on either cell growth or differentiation.

Further, the effect of the mediator appears to be specific to certain stages of erythroid progenitor cells, in that the macrophage mediator inhibited the growth and erythroid differentiation of uncommitted stem cells more than that of erythroid committed cells which were induced by treatment with $Me_2SO$, HMBA, butyric acid or hypoxanthine. The inhibitory effect of the macrophage mediator on cell growth was more pronounced in cells growing logarithmically at a constant rate. Hemin treatment of Friend cells is known to cause erythroid cell maturation leading to the appearance of hemoglobinized cells but without accompanying the commitment of undifferentiated stem cells to the erythroid precursor cells (Gusella, J, F., Weil, S, C., Tsiftsoglon, A. S., Volloch, V., Neuman, J. R. and Housman, D. (1976) Blood 56:481–487). Interestingly, the endotoxin-stimulated macrophage mediator also had very little effect on the growth and differentiation of Friend cells in the presence of hemin.

These results indicate that the endotoxin-stimulated macrophage mediator exerts its inhibitory effect on the growth and differentiation of cells of erythroid precursor cells including those which have been committed to undergo erythroid differentiation. On the other hand, cells which have fully expressed characteristics of erythroid cells such as increased activities of ALA dehydratase and PBG deaminase, and increased contents of protoporphyrin and heme are no longer sensitive to the inhibitory effect of the conditioned medium. Thus it appears that the action of the endotoxin-stimulated conditioned medium is relatively specific to certain early stages of erythroid precursor cells but not to fully differentiated erythroid cells.

We have also attempted to purify the mediator from the endotoxin-stimulated macrophage conditioned medium and found that a highly purified mediator retained the inhibitory property both on lipoprotein lipase activity in 3T3 cells and on the growth and differentiation of Friend cells.

The macrophage factor described in this Example is believed to play a role in the pathogenesis of the anemia associated with endotoxemia or other chronic disease states, e.g., cancer, rheumatoid arthritis, where the activity of the reticuloendothelia system is stimulated. The Friend cell system described here should be useful to detect such in vivo mediators and to elucidate the biochemical basis for the cellular effect of the mediator(s). This assay system should also aid the isolation of this factor and the identification of its relationship with other immune cell factors which are produced in response to invasion.

We claim:

1. A method for treating an adverse effect in a human of the about 70 kDa mediator substance which results from endotoxin stimulation of macrophages and which has the biological activity of suppression of lipoprotein lipase activity, said method comprising administering an antibody specifically reactive with said about 70 kDa mediator in an amount effective to neutralize suppression of an anabolic enzyme selected from the group consisting of lipoprotein lipase, acetyl coA carboxylase and fatty acid synthetase, said suppression induced by said about 70 kDa mediator.

2. A method for treating an adverse effect in humans of the about 70 kDa mediator substance which results from endotoxin stimulation of macrophages and which has the biological activity of suppression of lipoprotein lipase activity, said method comprising administering an amount of an antibody capable of reducing inhibition of growth and differentiation of erythroid-committed cells wherein said inhibition is induced by said about 70 kDa mediator substance.

3. The method of claim 1 or 2 wherein said antibody is a monoclonal antibody.

4. The method of claim 1 or 2 wherein the adverse effect neutralized is suppression of the anabolic enzymes lipoprotein lipase, acetyl CoA carboxylase and fatty acid synthetase.

5. The method of claim 1 or 2 wherein the human is suffering from shock.

6. The method of claim 1 or 2 wherein the human is suffering from cacbexia.

7. The method of claim 1 or 2 wherein the human is suffering from anemia associated with a chronic disease state.

8. The method of claim 7 wherein the chronic disease state is rheumatoid arthritis.

\* \* \* \* \*

UNITED STATES PATENT AND TRADEMARK OFFICE
CERTIFICATE OF CORRECTION

PATENT NO.   : 6,419,927 B1
DATED        : July 16, 2002
INVENTOR(S)  : Anthony Cerami et al.

It is certified that error appears in the above-identified patent and that said Letters Patent is hereby corrected as shown below:

Column 1,
Lines 44-45, please delete "derangement" and insert -- derangements --.
Line 59, please delete "bodywas" and insert -- body was --.
Line 65, please insert a " ;" after "(1968)".

Column 2,
Line 34, please delete "Investigatlonof" and insert --Investigation of --.
Line 36, please delete "adversesequelae" and insert -- adverse sequelae --.
Line 45, please delete "areundergoing" and insert -- are undergoing --.
Line 48, please delete "amammal" and insert -- a mammal --.
Line 49, please delete "astimulator" and insert -- a stimulator --.
Line 50, please delete "Forexample" and insert -- For example --.
Line 51, please delete "Instanceof" and insert -- Instance of --.
Line 57, please delete "themacrophage" and insert -- the macrophage --.
Line 58, please delete "begathered" and insert -- be gathered --.
Line 64, please delete "theactivity" and insert -- the activity --.
Line 65, please delete "ofmedlator" and insert -- of mediator --.
Line 66, please delete "periodwhich" and insert -- period which --.

Column 3,
Line 4, please delete "sulfate" and insert -- sulfate. --.
Line 7, please delete "beenobserved" and insert -- been observed --.
Line 8, please delete "lipoproteinlipase" and insert -- lipoprotein lipase --.
Line 11, please delete "tobe" and insert -- to be --.
Line 15, please delete "thelike" and insert -- the like--.
Line 22, please delete "beprepared" and insert -- be prepared--.
Line 29, please delete "fromthe" and insert -- from the --.
Line 32, please delete "foundpresent" and insert -- found present --.
Line 35, please delete "instancewhere" and insert -- instance where --.
Line 37, please delete "observed.See" and insert -- observed. See --.
Line 43, please delete "Academl" and insert -- Academic --.
Line 45, please delete "wherespecific" and insert -- where specific --.
Line 51, please delete "mediatorsubstances " and insert -- mediator substances --.
Line 57, please delete "includlngthe" and insert -- including the --.
Line 48, please delete "musespleen" and insert -- mouse spleen --.

Column 4,
Line 7, please delete "mammals,comprising" and insert -- mammals, comprising --.
Line 8, please delete "ofa" and insert -- of a --.
Line 9, please delete "administeringan" and insert -- administering an --.
Line 10. please delete "toprevent" and insert -- to prevent --.
Line 18, please delete "thesynthesis" and insert -- the synthesis --.

UNITED STATES PATENT AND TRADEMARK OFFICE
CERTIFICATE OF CORRECTION

PATENT NO. : 6,419,927 B1
DATED : July 16, 2002
INVENTOR(S) : Anthony Cerami et al.

It is certified that error appears in the above-identified patent and that said Letters Patent is hereby corrected as shown below:

Column 4 (cont'd),
Line 21, please delete "instance,a" and insert -- Instance, specific --.
Line 25, please delete "fromthe" and insert -- from the --.
Line 26, please delete "ofadded" and insert -- of added --.
Line 30, please delete "substanceproductlon" and insert -- substance production --
Line 31, please delete "thedescrlptlon" and insert -- the description --
Line 32, please delete "theproduction" and insert -- the production --.
Line 35, please delete "withdexamethasone" and insert -- with dexamethasone --.
Line 42, please delete "thatthe" and insert -- that the --.
Line 43, please delete "substance," and insert -- substances, --.
Line 45, please delete "diagnosis.Further" and insert -- diagnosis. Further --.
Line 49, please delete "ofdrugs" and insert -- of drugs --.
Line 50, please delete "(capable" and insert -- capable --.
Line 50, please delete "theadverse" and insert -- the adverse --.
Line 63, please delete "substance" and insert -- substances --.
Line 64, please delete "incombating" and insert -- In combating --.

Column 5,
Line 1, please delete "substance" and insert -- substances --.
Line 5, please delete "description,which" and insert -- description, which --.
Line 6, please delete "Illustrativedrawings" and insert -- illustrative drawings --.
Line 12, please delete "Example," and insert -- Example 1, --.
Line 14, please delete "(+SEM)" and insert -- (±SEM) --.
Line 18, please delete "asthe" and insert -- as the --.
Line 25, please delete "llpoproteinlipase" and insert -- lipoprotein llpase --.
Line 26, please insert "±" before "SEM".
Line 29, please delete "activltlesof" and insert -- activities of --.
Line 32, please delete "DMIE" and insert -- DME --.
Line 45, please delete "cytosolicfractions" and insert -- cytosolic fractions --.
Line 48, please delete "Infra.Panel" and insert -- Infra. Panel --.
Line 54, please delete "percentof" and insert -- percent of --.
Line 55, please delete "afterexposure" and insert -- after exposure --.
Line 60, please delete "A:Autoradlogram" and insert -- A: Autoradiogram --.

Column 6,
Line 5, please delete "proteinpulse" and insert -- protein pulse, --.
Line 7, please delete "theremainder" and insert -- the remainder --.
Line 16, please delete "35S-methionine" and insert -- $^{35}$S-methionine --.
Line 18, please delete "mediator.3T3" and insert -- mediator. 3T3 --.
Line 21, please delete "tothe" and insert -- to the --.
Line 27, please insert a "." after "hours".
Line 32, please delete "modiator.Experimental" and insert -- mediator. Experimental. --.

UNITED STATES PATENT AND TRADEMARK OFFICE
CERTIFICATE OF CORRECTION

PATENT NO.    : 6,419,927 B1
DATED         : July 16, 2002
INVENTOR(S)   : Anthony Cerami et al.

It is certified that error appears in the above-identified patent and that said Letters Patent is hereby corrected as shown below:

Column 6 (cont'),
Line 33, please delete "legendto" and insert -- legend to --.
Line 40, please delete "cellsnot" and insert -- cells not --.
Line 44, please delete "inFriend" and insert -- in Friend --.
Line 49, please delete "endotoxin(5µg/ml)" and insert -- endotoxin (5µg/ml) --.
Line 52, please delete "controlculture" and insert -- control culture --.
Line 59, please delete "was8" and insert -- was 8 --.
Line 65, please delete "andintermediates" and insert -- and intermediates --.
Line 66, please delete "infra.Data" and insert -- infra. Data --.

Column 7,
Line 3, please delete "anderythroid" and insert -- and erythrold --.
Line 8, please delete "theabscissa" and insert -- the abscissa --.
Line 10, please delete "hemeand" and insert -- heme and --.
Line 11, please delete "Incucbationas" and insert -- incubation as --.
Line 12, please delete "duplicatedeterminations" and insert -- duplicate determinations --.
Line 13, please delete "MeSo" and insert -- $Me_2SO$ --.
Line 26, please delete "Frlendcells" and insert -- Friend cells --.
Line 45, please delete "bymammallan" and insert -- by mammalian --.
Line 46, please delete "referto" and insert -- refer to --.
Line 49, please delete "observedthat" and insert -- observed that --.
Line 49, please delete "substance causes" and insert -- substances cause --.
Line 51, please delete "acatabolic" and insert -- a catabolic --.
Line 53, please delete "lipoproteinlipase" and insert -- lipoprotein lipase --.
Line 54, please delete "listedearller" and insert -- listed earlier --.
Line 58, please delete "inresponse" and insert -- In response --.
Line 59, please delete "thoselisted" and insert -- those listed --.
Line 61, please delete "asadipose" and insert -- asadipose --.
Line 61, please delete "liver,and" and insert -- liver, and --.
Line 62, please delete "impendingneed" and insert -- impending need --.
Line 63, please delete "themedlator" and insert -- the mediator --.
Line 65, please delete "supplyof" and insert -- supply of --.
Line 66, please delete "themammal" and insert -- the mammal --.
Line 67, please delete "stores;" and insert -- stored; --.

Column 8,
Line 11, please delete "anextended" and insert -- an extended --.
Line 13, please delete "theinvention" and insert -- the invention --.
Line 17, please delete "theways" and insert -- the ways --.
Line 21, please delete "drawnoff" and insert -- drawn off --.
Line 22, please delete "witha" and insert -- with a --.
Line 24, please delete "particularmethod" and insert -- particular method --.

UNITED STATES PATENT AND TRADEMARK OFFICE
CERTIFICATE OF CORRECTION

PATENT NO. : 6,419,927 B1
DATED : July 16, 2002
INVENTOR(S) : Anthony Cerami et al.

It is certified that error appears in the above-identified patent and that said Letters Patent is hereby corrected as shown below:

Column 8 (cont'd),
Line 25, please delete "skillof" and insert -- skill of --.
Line 30, please delete "thepresence" and insert -- the presence --.
Line 34, please delete "thehybridoma" and insert -- the hybrldoma --.
Line 35, please delete "spleenlymphocyles" and Insert -- spleen lymphocyles --.
Line 36, please delete "bystandard" and insert -- by standard --.
Line 37, please delete "of mediator substances" and insert -- of the mediator substance --.
Lines 41-42, please delete "determinethe" and insert -- determine the --.
Line 43, please delete "mammalianbody" and insert -- mammalian body --.
Line 44, please delete "presenceof" and insert -- presence of --.
Line 47, please delete "theantibody" and insert -- the antibody --.
lute 48, please delete "toas" and insert -- to as --.
Line 52, please delete "canbe" and insert -- can be --.
Line 53, please delete "tosuch" and insert -- to such --.
Line 54, please delete "known.Three" and insert -- known. Three --.
Line 55, please delete "elthermediator" and insert -- either mediator --.

Column 9,
Line 7, please delete "complexis" and insert -- complex is --.
Line 8, please delete "hasformed" and insert -- has formed --.
Line 18, please delete "thisdescription" and insert -- this description --.
Line 25, please delete "whenexposed" and insert -- when exposed --.
Line 30, please delete "throughon" and insert -- through on --.
Line 33, please delete "canbe" and insert -- can be --.
Line 36, please delete "calorimetric" and insert -- colorimetric --.
Line 47, please delete "materialsHlgh" and insert -- materials. High --.
Line 48, please delete "bodymay" and insert -- body may --.
Line 49, please delete "Theantibody(ies)" and insert -- The antibody(ies) --.
Line 52, please delete "doseof" and insert -- dose of --.
Line 53, please delete "mediator.The" and insert -- mediator. The --.
Line 55, please delete "wellknown" and insert -- well known --.
Line 56, please delete "age,weight" and insert -- age, weight --.
Line 57, please delete "themediator" and insert -- the mediator --.
Line 62, please delete "techniquesdiscussed" and insert -- techniques discussed --.
Line 63, please delete "thelabeled" and insert -- the labeled --.
Line 64, please delete "specificthereto" and insert -- specific thereto --.

Column 10,
Line 15, please delete "comprising (a)" and insert -- comprising: (a) --.
Line 24, please delete "suchmodifications" and insert -- such modifications --.
Line 38, please delete "effectsof" and insert -- effects of --.
Line 46, please delete "andthe" and insert -- and the --.

UNITED STATES PATENT AND TRADEMARK OFFICE
CERTIFICATE OF CORRECTION

PATENT NO.   : 6,419,927 B1
DATED        : July 16, 2002
INVENTOR(S)  : Anthony Cerami et al.

It is certified that error appears in the above-identified patent and that said Letters Patent is hereby corrected as shown below:

Column 10 (cont'd),
Line 51, please delete "a obesity" and insert -- as obesity --.
Line 54, please delete "synthease" and insert -- sythetase --.

Column 11,
Line 7, please delete "Whilethe" and insert -- While the --.
Line 8, please delete "thepresent" and insert -- the present --.
Line 13, please delete "ofsuch" and insert -- of such --.
Line 28, please delete "Oncethe" and insert -- Once the --
Line 29, please delete "tohave" and insert -- to have --.

Column 12,
Line 18, please delete "Exp.Biol." and insert -- Exp. Biol --.
Line 28, please delete "sterilepolypropylene" and insert -- sterile polypropylene --.
Line 29, please delete "Bector" and insert -- Becton --.
Line 29, please delete "Cockoysville" and insert -- Cocheysville -- .
Line 30, please delete "DDME" and insert -- DME --.
Line 50, please delete "tocompare" and insert -- to compare --.
Line 51, please delete "aspercent" and insert -- as percent --.
Line 52, please delete "rangeobserved" and insert -- range observed --.
Line 53, please delete "tissue.Unless" and insert -- tissue. Unless --.
Line 67, please delete "imp" and insert -- i.p. --.

Column 13,
Line 3, please delete "obtainedby" and insert -- obtained by --.
Line 11, please delete "dishwere" and insert -- dish were --.
Line 13, please delete "thecells" and insert -- the cells --.
Line 25, please delete "ofendotoxin" and insert -- of endotoxin --.
Line 26, please delete "eithersaline" and insert -- either saline --.
Line 28, please delete "strainof" and insert -- strain of --.
Line 29, please delete "daysafter" and insert -- days after --.
Lines 30-31, please delete "adiposetissue" and insert -- adipose tissue --.
Line 33, please delete "theserum" and insert -- the serum --.
Lines 40 and 44, please delete "endotoxin-sensitivemice" and insert -- endotoxin-sensitive mice --.
Line 45, please delete "LPLactivity" and insert -- LPL activity --.
Line 49, please delete "theseanimals" and insert -- these animals --.
Line 55, please delete "ofthe" and insert -- of the --.
Line 62, please delete "effectand" and insert -- effect and --.
Line 64, please delete "thissmall" and insert -- this small --.

UNITED STATES PATENT AND TRADEMARK OFFICE
CERTIFICATE OF CORRECTION

PATENT NO.     : 6,419,927 B1
DATED           : July 16, 2002
INVENTOR(S)  : Anthony Cerami et al.

It is certified that error appears in the above-identified patent and that said Letters Patent is hereby corrected as shown below:

Column 14,
Line 5, please delete "endotoxinsuppresses" and insert -- endotoxin suppresses --.
Line 10, please delete "ofC3H/HeJ" and insert -- of C3H/HeJ --.
Line 16, please delete "dlfferencein" and insert -- difference in --.
Line 19, please delete "asmall" and insert -- a small --.
Line 27, please delete "Thisaction" and insert -- This action --.
Line 28, please delete "suppressadipose" and insert -- suppress adipose--.
Line 29, please delete "aswell" and insert -- as well --.
Line 30, please delete "cellssensltive" and insert -- cells sensltlve --.
Line 31, please add a "." after "mediator".
Line 47, please delete "mediatoractive" and insert -- mediator active --.
Line 54, please delete "fractionseluting" and insert --fractions eluting --.
Line 60, please delete "molecularweight" and insert -- molecular weight --.
Line 65, please delete "thlsprocedure" and insert -- this procedure --.

Column 15,
Line 1, please delete "Millexmembrane" and insert -- Millex membrane --.

Column18,
Line 14, please delete "onditions" and insert -- conditions--.
Line 41, please delete "IGG" and insert -- IgG --.

Column 19,
Line 55, please delete "5-1" and insert -- 5 $\mu$l --.

Column 20,
Line 61, please delete "change observed, while" and insert -- change observed. While --.

Signed and Sealed this

First Day of June, 2004

JON W. DUDAS
*Acting Director of the United States Patent and Trademark Office*

Disclaimer 6,419,927—Anthony Cerami, Shelter Island, NY. METHOD FOR REDUCING ADVERSE EFFECTS OF A HUMAN 70KDA MEDIATOR WHICH RESULTS FROM ENDOTOXIN STIMULATION OF MACROPHAGES. Patent dated July 16, 2002. Disclaimer filed April 23, 2004, by the inventor Anthony Cerami.

The term of this patent shall not extend beyond the expiration date of Pat. Nos. 5,698,419 and 5,700,466.

(*Official Gazette March 22, 2005*)